United States Patent
Petisce et al.

(10) Patent No.: US 10,610,140 B2
(45) Date of Patent: Apr. 7, 2020

(54) OXYGEN ENHANCING MEMBRANE SYSTEMS FOR IMPLANTABLE DEVICES

(71) Applicant: DexCom, Inc., San Diego, CA (US)

(72) Inventors: James R. Petisce, Westford, MA (US); Mark A. Tapsak, Bloomsburg, PA (US); Peter C. Simpson, Cardiff, CA (US); Victoria Carr-Brendel, Edina, MN (US); James H. Brauker, Coldwater, MI (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 15/977,927

(22) Filed: May 11, 2018

(65) Prior Publication Data

US 2018/0256084 A1 Sep. 13, 2018

Related U.S. Application Data

(63) Continuation of application No. 15/429,022, filed on Feb. 9, 2017, now Pat. No. 9,993,186, which is a
(Continued)

(51) Int. Cl.
*A61B 5/1473* (2006.01)
*A61B 5/1468* (2006.01)
(Continued)

(52) U.S. Cl.
CPC .......... *A61B 5/1473* (2013.01); *A61B 5/1468* (2013.01); *A61B 5/14532* (2013.01);
(Continued)

(58) Field of Classification Search
CPC .............. A61B 5/1473; A61B 5/14532; A61B 5/14546; A61B 5/1468; A61B 5/14735;
(Continued)

(56) References Cited

U.S. PATENT DOCUMENTS

| | | |
|---|---|---|
| 2,830,020 A | 4/1958 | Christmann et al. |
| 3,220,960 A | 11/1965 | Wichterle et al. |

(Continued)

FOREIGN PATENT DOCUMENTS

| | | |
|---|---|---|
| EP | 0 098 592 | 1/1984 |
| EP | 0 127 958 | 12/1984 |

(Continued)

OTHER PUBLICATIONS

Aalders et al. 1991. Development of a wearable glucose sensor; studies in healthy volunteers and in diabetic patients. The International Journal of Artificial Organs 14(2):102-108.
(Continued)

*Primary Examiner* — Navin Natnithithadha
(74) *Attorney, Agent, or Firm* — Knobbe, Martens, Olson & Bear, LLP

(57) ABSTRACT

The present invention relates generally to systems and methods for increasing oxygen availability to implantable devices. The preferred embodiments provide a membrane system configured to provide protection of the device from the biological environment and/or a catalyst for enabling an enzymatic reaction, wherein the membrane system includes a polymer formed from a high oxygen soluble material. The high oxygen soluble polymer material is disposed adjacent to an oxygen-utilizing source on the implantable device so as to dynamically retain high oxygen availability to the oxygen-utilizing source during oxygen deficits. Membrane systems of the preferred embodiments are useful for implantable devices with oxygen-utilizing sources and/or that function in low oxygen environments, such as enzyme-based electrochemical sensors and cell transplantation devices.

64 Claims, 5 Drawing Sheets

Related U.S. Application Data continuation of application No. 14/529,034, filed on Oct. 30, 2014, now Pat. No. 9,597,027, which is a continuation of application No. 13/187,277, filed on Jul. 20, 2011, now Pat. No. 8,909,314, which is a continuation of application No. 11/410,392, filed on Apr. 25, 2006, now Pat. No. 8,255,033, which is a continuation of application No. 10/896,639, filed on Jul. 21, 2004, now Pat. No. 7,379,765.

(60) Provisional application No. 60/490,009, filed on Jul. 25, 2003.

(51) Int. Cl.
*A61B 5/1486* (2006.01)
*A61B 5/145* (2006.01)
*C12Q 1/00* (2006.01)

(52) U.S. Cl.
CPC ...... *A61B 5/14546* (2013.01); *A61B 5/14735* (2013.01); *A61B 5/14865* (2013.01); *C12Q 1/002* (2013.01); *C12Q 1/006* (2013.01); *A61B 5/145* (2013.01); *A61B 5/14503* (2013.01)

(58) Field of Classification Search
CPC . A61B 5/14865; A61B 5/145; A61B 5/14503; C12Q 1/002; C12Q 1/006
USPC .......................................... 600/309, 345–366
See application file for complete search history.

(56) References Cited

U.S. PATENT DOCUMENTS

| | | |
|---|---|---|
| 3,562,352 A | 2/1971 | Nyilas |
| 3,607,329 A | 9/1971 | Manjikian |
| 3,746,588 A | 7/1973 | Brown, Jr. |
| 3,898,984 A | 8/1975 | Mandel et al. |
| 3,943,918 A | 3/1976 | Lewis |
| 4,003,621 A | 1/1977 | Lamp |
| 4,136,250 A | 1/1979 | Mueller et al. |
| 4,253,469 A | 3/1981 | Aslan |
| 4,256,561 A | 3/1981 | Schindler et al. |
| 4,260,725 A | 4/1981 | Keogh et al. |
| 4,267,145 A | 5/1981 | Wysong |
| 4,292,423 A | 9/1981 | Kaufmann et al. |
| 4,353,888 A | 10/1982 | Sefton |
| 4,374,013 A | 2/1983 | Enfors |
| 4,403,984 A | 9/1983 | Ash et al. |
| 4,415,666 A | 11/1983 | D'Orazio et al. |
| 4,431,507 A | 2/1984 | Nankai et al. |
| 4,442,841 A | 4/1984 | Uehara et al. |
| 4,454,295 A | 6/1984 | Wittmann et al. |
| 4,482,666 A | 11/1984 | Reeves |
| 4,484,987 A | 11/1984 | Gough |
| 4,493,714 A | 1/1985 | Ueda et al. |
| 4,494,950 A | 1/1985 | Fischell |
| 4,527,999 A | 7/1985 | Lee |
| 4,545,382 A | 10/1985 | Higgins et al. |
| 4,554,927 A | 11/1985 | Fussell |
| 4,602,922 A | 7/1986 | Cabasso et al. |
| 4,632,968 A | 12/1986 | Yokota et al. |
| 4,644,046 A | 2/1987 | Yamada |
| 4,647,643 A | 3/1987 | Zdrabala et al. |
| 4,650,547 A | 3/1987 | Gough |
| 4,671,288 A | 6/1987 | Gough |
| 4,672,970 A | 6/1987 | Uchida et al. |
| 4,680,268 A | 7/1987 | Clark, Jr. |
| 4,684,538 A | 8/1987 | Klemarczyk |
| 4,685,463 A | 8/1987 | Williams |
| 4,686,044 A | 8/1987 | Behnke et al. |
| 4,686,137 A | 8/1987 | Ward, Jr. et al. |
| 4,689,149 A | 8/1987 | Kanno et al. |
| 4,703,756 A | 11/1987 | Gough et al. |
| 4,711,245 A | 12/1987 | Higgins et al. |
| 4,721,677 A | 1/1988 | Clark, Jr. |
| 4,726,381 A | 2/1988 | Jones |
| 4,731,726 A | 3/1988 | Allen, III |
| 4,739,380 A | 4/1988 | Lauks et al. |
| 4,757,022 A | 7/1988 | Shults et al. |
| 4,763,658 A | 8/1988 | Jones |
| 4,781,733 A | 11/1988 | Babcock et al. |
| 4,786,657 A | 11/1988 | Hammar et al. |
| 4,793,555 A | 12/1988 | Lee et al. |
| 4,803,243 A | 2/1989 | Fujimoto et al. |
| 4,805,625 A | 2/1989 | Wyler |
| 4,813,424 A | 3/1989 | Wilkins |
| 4,822,336 A | 4/1989 | DiTraglia |
| 4,823,808 A | 4/1989 | Clegg et al. |
| 4,832,034 A | 5/1989 | Pizziconi et al. |
| 4,852,573 A | 8/1989 | Kennedy |
| 4,861,830 A | 8/1989 | Ward, Jr. |
| 4,871,440 A | 10/1989 | Nagata et al. |
| 4,880,883 A | 11/1989 | Grasel et al. |
| 4,886,740 A | 12/1989 | Vadgama |
| 4,890,620 A | 1/1990 | Gough |
| 4,908,208 A | 3/1990 | Lee et al. |
| 4,909,908 A | 3/1990 | Ross et al. |
| 4,919,141 A | 4/1990 | Zier et al. |
| 4,938,860 A | 7/1990 | Wogoman |
| 4,951,657 A | 8/1990 | Pfister et al. |
| 4,952,618 A | 8/1990 | Olsen |
| 4,953,552 A | 9/1990 | DeMarzo |
| 4,954,381 A | 9/1990 | Cabasso et al. |
| 4,960,594 A | 10/1990 | Honeycutt |
| 4,961,954 A | 10/1990 | Goldberg et al. |
| 4,970,145 A | 11/1990 | Bennetto et al. |
| 4,973,320 A | 11/1990 | Brenner et al. |
| 4,988,341 A | 1/1991 | Columbus et al. |
| 4,994,167 A | 2/1991 | Shults et al. |
| 5,002,590 A | 3/1991 | Friesen et al. |
| 5,010,141 A | 4/1991 | Mueller |
| 5,034,461 A | 7/1991 | Lai et al. |
| 5,045,601 A | 9/1991 | Capelli et al. |
| 5,050,612 A | 9/1991 | Matsumura |
| 5,063,081 A | 11/1991 | Cozzette et al. |
| 5,070,169 A | 12/1991 | Robertson et al. |
| 5,071,452 A | 12/1991 | Avrillon et al. |
| 5,094,876 A | 3/1992 | Goldberg et al. |
| 5,100,689 A | 3/1992 | Goldberg et al. |
| 5,108,819 A | 4/1992 | Heller et al. |
| 5,115,056 A | 5/1992 | Mueller et al. |
| 5,120,813 A | 6/1992 | Ward, Jr. |
| 5,128,408 A | 7/1992 | Tanaka et al. |
| 5,135,297 A | 8/1992 | Valint, Jr. |
| 5,137,028 A | 8/1992 | Nishimura |
| 5,147,725 A | 9/1992 | Pinchuk |
| 5,155,149 A | 10/1992 | Atwater et al. |
| 5,160,418 A | 11/1992 | Mullen |
| 5,165,407 A | 11/1992 | Wilson et al. |
| 5,169,906 A | 12/1992 | Cray et al. |
| 5,171,689 A | 12/1992 | Kawaguri et al. |
| 5,183,549 A | 2/1993 | Joseph et al. |
| 5,200,051 A | 4/1993 | Cozzette et al. |
| 5,202,261 A | 4/1993 | Musho et al. |
| 5,208,313 A | 5/1993 | Krishnan |
| 5,212,050 A | 5/1993 | Mier et al. |
| 5,219,965 A | 6/1993 | Valint et al. |
| 5,221,724 A | 6/1993 | Li et al. |
| 5,242,835 A | 9/1993 | Jensen |
| 5,249,576 A | 10/1993 | Goldberger et al. |
| 5,250,439 A | 10/1993 | Musho et al. |
| 5,262,305 A | 11/1993 | Heller et al. |
| 5,264,104 A | 11/1993 | Gregg et al. |
| 5,269,891 A | 12/1993 | Colin |
| 5,284,140 A | 2/1994 | Allen et al. |
| 5,286,364 A | 2/1994 | Yacynych et al. |
| 5,296,144 A | 3/1994 | Sternina et al. |
| 5,299,571 A | 4/1994 | Mastrototaro |
| 5,302,440 A | 4/1994 | Davis |
| 5,316,008 A | 5/1994 | Suga et al. |
| 5,322,063 A | 6/1994 | Allen et al. |
| 5,324,322 A | 6/1994 | Grill, Jr. et al. |
| 5,331,555 A | 7/1994 | Hashimoto et al. |

(56) References Cited

U.S. PATENT DOCUMENTS

| | | |
|---|---|---|
| 5,334,681 A | 8/1994 | Mueller et al. |
| 5,336,102 A | 8/1994 | Cairns et al. |
| 5,342,693 A | 8/1994 | Winters et al. |
| 5,352,348 A | 10/1994 | Young et al. |
| 5,376,400 A | 12/1994 | Goldberg et al. |
| 5,384,028 A | 1/1995 | Ito |
| 5,387,327 A | 2/1995 | Khan |
| 5,387,329 A | 2/1995 | Foos et al. |
| 5,390,671 A | 2/1995 | Lord et al. |
| 5,391,250 A | 2/1995 | Cheney, II et al. |
| 5,397,451 A | 3/1995 | Senda et al. |
| 5,401,376 A | 3/1995 | Foos et al. |
| 5,411,866 A | 5/1995 | Luong et al. |
| 5,417,395 A | 5/1995 | Fowler et al. |
| 5,426,158 A | 6/1995 | Mueller et al. |
| 5,428,123 A | 6/1995 | Ward et al. |
| 5,429,735 A | 7/1995 | Johnson et al. |
| 5,438,984 A | 8/1995 | Schoendorfer |
| 5,453,248 A | 9/1995 | Olstein |
| 5,462,051 A | 10/1995 | Oka et al. |
| 5,462,064 A | 10/1995 | D'Angelo et al. |
| 5,466,575 A | 11/1995 | Cozzette et al. |
| 5,469,846 A | 11/1995 | Khan |
| 5,476,094 A | 12/1995 | Allen et al. |
| 5,482,473 A | 1/1996 | Lord et al. |
| 5,494,562 A | 2/1996 | Maley et al. |
| 5,497,772 A | 3/1996 | Schulman et al. |
| 5,503,719 A | 4/1996 | Foos et al. |
| 5,507,288 A | 4/1996 | Bocker et al. |
| 5,513,636 A | 5/1996 | Palti |
| 5,518,601 A | 5/1996 | Foos et al. |
| 5,521,273 A | 5/1996 | Yilgor et al. |
| 5,531,878 A | 7/1996 | Vadgama et al. |
| 5,541,305 A | 7/1996 | Yokota et al. |
| 5,545,223 A | 8/1996 | Neuenfeldt et al. |
| 5,549,675 A | 8/1996 | Neuenfeldt et al. |
| 5,552,112 A | 9/1996 | Schiffmann et al. |
| 5,554,339 A | 9/1996 | Cozzette |
| 5,564,439 A | 10/1996 | Picha |
| 5,568,806 A | 10/1996 | Cheney, II et al. |
| 5,569,186 A | 10/1996 | Lord et al. |
| 5,575,930 A | 11/1996 | Tietje-Girault et al. |
| 5,582,184 A | 12/1996 | Ericson et al. |
| 5,584,813 A | 12/1996 | Livingston et al. |
| 5,584,876 A | 12/1996 | Bruchman et al. |
| 5,586,553 A | 12/1996 | Halili et al. |
| 5,589,563 A | 12/1996 | Ward et al. |
| 5,593,440 A | 1/1997 | Brauker et al. |
| 5,593,852 A | 1/1997 | Heller et al. |
| 5,595,646 A | 1/1997 | Foos et al. |
| 5,611,900 A | 3/1997 | Worden |
| 5,624,537 A | 4/1997 | Turner et al. |
| 5,631,340 A | 5/1997 | Olstein |
| 5,640,954 A | 6/1997 | Pfeiffer |
| 5,653,756 A | 8/1997 | Clarke et al. |
| 5,665,222 A | 9/1997 | Heller et al. |
| 5,670,097 A | 9/1997 | Duan et al. |
| 5,683,562 A | 11/1997 | Schaffer et al. |
| 5,695,623 A | 12/1997 | Michel et al. |
| 5,700,559 A | 12/1997 | Sheu et al. |
| 5,702,823 A | 12/1997 | Forrestal et al. |
| 5,703,359 A | 12/1997 | Wampler, III |
| 5,713,888 A | 2/1998 | Neuenfeldt et al. |
| 5,733,336 A | 3/1998 | Neuenfeldt et al. |
| 5,738,902 A | 4/1998 | Forrestal et al. |
| 5,741,330 A | 4/1998 | Brauker et al. |
| 5,743,262 A | 4/1998 | Lepper, Jr. et al. |
| 5,746,898 A | 5/1998 | Priedel |
| 5,756,632 A | 5/1998 | Ward et al. |
| 5,760,155 A | 6/1998 | Mowrer et al. |
| 5,766,839 A | 6/1998 | Johnson et al. |
| 5,773,270 A | 6/1998 | D'Orazio et al. |
| 5,776,324 A | 7/1998 | Usala |
| 5,777,060 A | 7/1998 | Van Antwerp |
| 5,782,912 A | 7/1998 | Brauker et al. |
| 5,786,439 A | 7/1998 | Van Antwerp et al. |
| 5,787,900 A | 8/1998 | Butler et al. |
| 5,791,344 A | 8/1998 | Schulman et al. |
| 5,795,453 A | 8/1998 | Gilmartin |
| 5,795,774 A | 8/1998 | Matsumoto et al. |
| 5,800,420 A | 9/1998 | Gross et al. |
| 5,800,529 A | 9/1998 | Brauker et al. |
| 5,804,048 A | 9/1998 | Wong et al. |
| 5,807,375 A | 9/1998 | Gross et al. |
| 5,807,406 A | 9/1998 | Brauker et al. |
| 5,807,636 A | 9/1998 | Sheu et al. |
| 5,820,570 A | 10/1998 | Erickson et al. |
| 5,820,622 A | 10/1998 | Gross et al. |
| 5,834,583 A | 11/1998 | Hancock et al. |
| 5,837,377 A | 11/1998 | Shen et al. |
| 5,837,454 A | 11/1998 | Cozzette et al. |
| 5,837,661 A | 11/1998 | Evans et al. |
| 5,843,069 A | 12/1998 | Butler et al. |
| 5,863,972 A | 1/1999 | Beckelmann et al. |
| 5,882,354 A | 3/1999 | Brauker et al. |
| 5,882,494 A | 3/1999 | Van Antwerp |
| 5,885,566 A | 3/1999 | Goldberg |
| 5,897,955 A | 4/1999 | Drumheller |
| 5,914,182 A | 6/1999 | Blubaugh, Jr. et al. |
| 5,931,814 A | 8/1999 | Alex et al. |
| 5,932,299 A | 8/1999 | Katoot |
| 5,945,498 A | 8/1999 | Hopken et al. |
| 5,947,127 A | 9/1999 | Tsugaya et al. |
| 5,954,643 A | 9/1999 | Van Antwerp et al. |
| 5,955,066 A | 9/1999 | Sako et al. |
| 5,957,854 A | 9/1999 | Besson et al. |
| 5,959,191 A | 9/1999 | Lewis et al. |
| 5,961,451 A | 10/1999 | Reber et al. |
| 5,964,261 A | 10/1999 | Neuenfeldt et al. |
| 5,964,993 A | 10/1999 | Blubaugh et al. |
| 5,965,380 A | 10/1999 | Heller et al. |
| 5,969,076 A | 10/1999 | Lai et al. |
| 5,972,199 A | 10/1999 | Heller et al. |
| 5,977,241 A | 11/1999 | Koloski et al. |
| 5,985,129 A | 11/1999 | Gough et al. |
| 5,999,848 A | 12/1999 | Gord et al. |
| 6,001,067 A | 12/1999 | Shults et al. |
| 6,002,954 A | 12/1999 | Van Antwerp et al. |
| 6,007,845 A | 12/1999 | Domb et al. |
| 6,011,984 A | 1/2000 | Van Antwerp et al. |
| 6,018,013 A | 1/2000 | Yoshida et al. |
| 6,018,033 A | 1/2000 | Chen et al. |
| 6,022,463 A | 2/2000 | Leader et al. |
| 6,030,827 A | 2/2000 | Davis et al. |
| 6,039,913 A | 3/2000 | Hirt et al. |
| 6,043,328 A | 3/2000 | Domschke et al. |
| 6,051,389 A | 4/2000 | Ahl et al. |
| 6,059,946 A | 5/2000 | Yukawa et al. |
| 6,066,448 A | 5/2000 | Wohlstadter et al. |
| 6,071,406 A | 6/2000 | Tsou |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,093,172 A | 7/2000 | Funderburk et al. |
| 6,119,028 A | 9/2000 | Schulman et al. |
| 6,121,009 A | 9/2000 | Heller et al. |
| 6,122,536 A | 9/2000 | Sun et al. |
| 6,134,461 A | 10/2000 | Say et al. |
| 6,162,611 A | 12/2000 | Heller et al. |
| 6,175,752 B1 | 1/2001 | Say et al. |
| 6,187,062 B1 | 2/2001 | Oweis et al. |
| 6,200,772 B1 | 3/2001 | Vadgama et al. |
| 6,212,416 B1 | 4/2001 | Ward et al. |
| 6,233,471 B1 | 5/2001 | Berner et al. |
| 6,241,863 B1 | 6/2001 | Monbouquette |
| 6,248,067 B1 | 6/2001 | Causey, III et al. |
| 6,254,586 B1 | 7/2001 | Mann et al. |
| 6,256,522 B1 | 7/2001 | Schultz |
| 6,259,937 B1 | 7/2001 | Schulman et al. |
| 6,264,825 B1 | 7/2001 | Blackburn et al. |
| 6,271,332 B1 | 8/2001 | Lohmann et al. |
| 6,284,478 B1 | 9/2001 | Heller et al. |
| 6,300,002 B1 | 10/2001 | Webb et al. |

(56) References Cited

U.S. PATENT DOCUMENTS

| | | |
|---|---|---|
| 6,303,670 B1 | 10/2001 | Fujino et al. |
| 6,306,594 B1 | 10/2001 | Cozzette |
| 6,312,706 B1 | 11/2001 | Lai et al. |
| 6,329,161 B1 | 12/2001 | Heller et al. |
| 6,329,488 B1 | 12/2001 | Terry et al. |
| 6,343,225 B1 | 1/2002 | Clark, Jr. |
| 6,358,557 B1 | 3/2002 | Wang et al. |
| 6,368,658 B1 | 4/2002 | Schwarz et al. |
| 6,372,020 B2 | 4/2002 | Hong et al. |
| 6,387,379 B1 | 5/2002 | Goldberg et al. |
| 6,395,325 B1 | 5/2002 | Hedge et al. |
| 6,405,066 B1 | 6/2002 | Essenpreis et al. |
| 6,407,195 B2 | 6/2002 | Sherman et al. |
| 6,413,393 B1 | 7/2002 | Van Antwerp et al. |
| 6,442,413 B1 | 8/2002 | Silver |
| 6,461,496 B1 | 10/2002 | Feldman et al. |
| 6,466,810 B1 | 10/2002 | Ward et al. |
| 6,484,046 B1 | 11/2002 | Say et al. |
| 6,512,939 B1 | 1/2003 | Colvin, Jr. et al. |
| 6,514,718 B2 | 2/2003 | Heller et al. |
| 6,528,584 B2 | 3/2003 | Kennedy et al. |
| 6,551,496 B1 | 4/2003 | Moles et al. |
| 6,554,982 B1 | 4/2003 | Shin et al. |
| 6,558,321 B1 | 5/2003 | Burd et al. |
| 6,565,509 B1 | 5/2003 | Say et al. |
| 6,579,498 B1 | 6/2003 | Eglise |
| 6,596,294 B2 | 7/2003 | Lai et al. |
| 6,618,934 B1 | 9/2003 | Feldman et al. |
| 6,633,772 B2 | 10/2003 | Ford et al. |
| 6,642,015 B2 | 11/2003 | Vachon et al. |
| 6,654,625 B1 | 11/2003 | Say et al. |
| 6,666,821 B2 | 12/2003 | Keimel |
| 6,670,115 B1 | 12/2003 | Zhang |
| 6,689,265 B2 | 2/2004 | Heller et al. |
| 6,692,528 B2 | 2/2004 | Ward et al. |
| 6,702,857 B2 | 3/2004 | Brauker et al. |
| 6,702,972 B1 | 3/2004 | Markle |
| 6,721,587 B2 | 4/2004 | Gough |
| 6,740,059 B2 | 5/2004 | Flaherty |
| 6,741,877 B1 | 5/2004 | Shults et al. |
| 6,784,274 B2 | 8/2004 | Van Antwerp et al. |
| 6,789,634 B1 | 9/2004 | Denton |
| 6,793,789 B2 | 9/2004 | Choi et al. |
| 6,801,041 B2 | 10/2004 | Karinka et al. |
| 6,802,957 B2 | 10/2004 | Jung et al. |
| 6,858,218 B2 | 2/2005 | Lai et al. |
| 6,862,465 B2 | 3/2005 | Shults et al. |
| 6,867,262 B1 | 3/2005 | Angel et al. |
| 6,875,386 B1 | 4/2005 | Ward et al. |
| 6,881,551 B2 | 4/2005 | Heller et al. |
| 6,895,263 B2 | 5/2005 | Shin et al. |
| 6,895,265 B2 | 5/2005 | Silver |
| 6,908,681 B2 | 6/2005 | Terry et al. |
| 6,932,894 B2 | 8/2005 | Mao et al. |
| 6,934,572 B2 | 8/2005 | Schulman et al. |
| 6,965,791 B1 | 11/2005 | Hitchcock et al. |
| 6,969,451 B2 | 11/2005 | Shin et al. |
| 6,973,706 B2 | 12/2005 | Say et al. |
| 7,008,979 B2 | 3/2006 | Schottman et al. |
| 7,014,948 B2 | 3/2006 | Lee et al. |
| 7,033,322 B2 | 4/2006 | Silver |
| 7,052,131 B2 | 5/2006 | McCabe et al. |
| 7,108,778 B2 | 9/2006 | Simpson et al. |
| 7,110,803 B2 | 9/2006 | Shults et al. |
| 7,118,667 B2 | 10/2006 | Lee |
| 7,120,483 B2 | 10/2006 | Russell et al. |
| 7,136,689 B2 | 11/2006 | Shults et al. |
| 7,153,265 B2 | 12/2006 | Vachon |
| 7,157,528 B2 | 1/2007 | Ward |
| 7,172,075 B1 | 2/2007 | Ji |
| 7,192,450 B2 | 3/2007 | Brauker et al. |
| 7,226,978 B2 | 6/2007 | Tapsak et al. |
| 7,229,471 B2 | 6/2007 | Gale et al. |
| 7,241,586 B2 | 7/2007 | Gulati et al. |
| 7,248,906 B2 | 7/2007 | Dirac et al. |
| 7,279,174 B2 | 10/2007 | Pacetti et al. |
| 7,303,814 B2 | 12/2007 | Lamberti et al. |
| 7,335,286 B2 | 2/2008 | Abel et al. |
| 7,336,984 B2 | 2/2008 | Gough et al. |
| 7,357,793 B2 | 4/2008 | Pacetti |
| 7,366,556 B2 | 4/2008 | Brister et al. |
| 7,379,765 B2 | 5/2008 | Petisce et al. |
| 7,417,164 B2 | 8/2008 | Suri |
| 7,423,074 B2 | 9/2008 | Lai et al. |
| 7,470,488 B2 | 12/2008 | Lee et al. |
| 7,507,579 B2 | 3/2009 | Boccazzi et al. |
| 7,534,330 B2 | 5/2009 | Yu et al. |
| 7,613,491 B2 | 11/2009 | Boock et al. |
| 7,651,596 B2 | 1/2010 | Petisce et al. |
| 7,687,586 B2 | 3/2010 | Ward et al. |
| 7,711,402 B2 | 5/2010 | Shults et al. |
| 7,792,562 B2 | 9/2010 | Shults et al. |
| 7,799,191 B2 | 9/2010 | Yu et al. |
| 7,828,728 B2 | 11/2010 | Boock et al. |
| 7,835,777 B2 | 11/2010 | Shults et al. |
| 7,860,545 B2 | 12/2010 | Shults et al. |
| 7,970,448 B2 | 6/2011 | Shults et al. |
| 8,255,030 B2 | 8/2012 | Petisce et al. |
| 8,255,032 B2 | 8/2012 | Petisce et al. |
| 8,255,033 B2 | 8/2012 | Petisce et al. |
| 8,909,314 B2 | 12/2014 | Petisce et al. |
| 9,597,027 B2 | 3/2017 | Petisce et al. |
| 2002/0018843 A1 | 2/2002 | Van Antwerp et al. |
| 2002/0043471 A1 | 4/2002 | Ikeda et al. |
| 2002/0055673 A1 | 5/2002 | Van Antwerp et al. |
| 2002/0123087 A1 | 9/2002 | Vachon et al. |
| 2002/0128546 A1 | 9/2002 | Silver |
| 2002/0133224 A1 | 9/2002 | Bajgar et al. |
| 2002/0156355 A1 | 10/2002 | Gough |
| 2002/0162792 A1 | 11/2002 | Zepf |
| 2002/0185384 A1 | 12/2002 | Leong et al. |
| 2003/0009093 A1 | 1/2003 | Silver |
| 2003/0023317 A1 | 1/2003 | Brauker et al. |
| 2003/0032874 A1 | 2/2003 | Rhodes et al. |
| 2003/0059631 A1 | 3/2003 | Al-Lamee |
| 2003/0065254 A1 | 4/2003 | Schulman et al. |
| 2003/0069383 A1 | 4/2003 | Van Antwerp et al. |
| 2003/0088166 A1 | 5/2003 | Say et al. |
| 2003/0096424 A1 | 5/2003 | Mao et al. |
| 2003/0104273 A1 | 6/2003 | Lee et al. |
| 2003/0125498 A1 | 7/2003 | McCabe et al. |
| 2003/0132227 A1 | 7/2003 | Geisler |
| 2003/0134100 A1 | 7/2003 | Mao et al. |
| 2003/0134347 A1 | 7/2003 | Heller et al. |
| 2003/0157409 A1 | 8/2003 | Huang et al. |
| 2003/0181794 A1 | 9/2003 | Rini et al. |
| 2003/0199745 A1 | 10/2003 | Burson et al. |
| 2003/0199878 A1 | 10/2003 | Pohjonen |
| 2003/0203991 A1 | 10/2003 | Schottman et al. |
| 2003/0211050 A1 | 11/2003 | Majeti et al. |
| 2003/0217966 A1 | 11/2003 | Tapsak et al. |
| 2003/0225324 A1 | 12/2003 | Anderson et al. |
| 2003/0228681 A1 | 12/2003 | Ritts et al. |
| 2003/0235817 A1 | 12/2003 | Bartkowiak et al. |
| 2004/0006263 A1 | 1/2004 | Anderson et al. |
| 2004/0011671 A1 | 1/2004 | Shults et al. |
| 2004/0045879 A1 | 3/2004 | Shults et al. |
| 2004/0063167 A1 | 4/2004 | Kaastrup et al. |
| 2004/0074785 A1 | 4/2004 | Holker |
| 2004/0077075 A1 | 4/2004 | Jensen et al. |
| 2004/0084306 A1 | 5/2004 | Shin et al. |
| 2004/0106741 A1 | 6/2004 | Kriesel et al. |
| 2004/0106857 A1 | 6/2004 | Gough |
| 2004/0111017 A1 | 6/2004 | Say et al. |
| 2004/0111144 A1 | 6/2004 | Lawin et al. |
| 2004/0120848 A1 | 6/2004 | Teodorczyk |
| 2004/0138543 A1 | 7/2004 | Russell et al. |
| 2004/0143173 A1 | 7/2004 | Reghabi et al. |
| 2004/0167801 A1 | 8/2004 | Say et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0213985 A1 | 10/2004 | Lee et al. |
| 2004/0224001 A1 | 11/2004 | Pacetti et al. |

(56) References Cited

U.S. PATENT DOCUMENTS

| | | |
|---|---|---|
| 2004/0228902 A1 | 11/2004 | Benz |
| 2004/0234575 A1 | 11/2004 | Horres et al. |
| 2005/0013842 A1 | 1/2005 | Qiu et al. |
| 2005/0031689 A1 | 2/2005 | Shults et al. |
| 2005/0032246 A1 | 2/2005 | Brennan et al. |
| 2005/0033132 A1 | 2/2005 | Shults et al. |
| 2005/0051440 A1 | 3/2005 | Simpson et al. |
| 2005/0054909 A1 | 3/2005 | Petisce et al. |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0089993 A1 | 4/2005 | Boccazzi et al. |
| 2005/0090607 A1 | 4/2005 | Tapsak et al. |
| 2005/0107677 A1 | 5/2005 | Ward et al. |
| 2005/0112169 A1 | 5/2005 | Brauker et al. |
| 2005/0112172 A1 | 5/2005 | Pacetti |
| 2005/0112358 A1 | 5/2005 | Potyrailo et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0124873 A1 | 6/2005 | Shults et al. |
| 2005/0139489 A1 | 6/2005 | Davies et al. |
| 2005/0154272 A1 | 7/2005 | Dirac et al. |
| 2005/0173245 A1 | 8/2005 | Feldman et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0184641 A1 | 8/2005 | Armitage et al. |
| 2005/0196747 A1 | 9/2005 | Stiene |
| 2005/0197554 A1 | 9/2005 | Polcha |
| 2005/0209665 A1 | 9/2005 | Hunter et al. |
| 2005/0233407 A1 | 10/2005 | Pamidi et al. |
| 2005/0239154 A1 | 10/2005 | Feldman et al. |
| 2005/0242479 A1 | 11/2005 | Petisce et al. |
| 2005/0245799 A1 | 11/2005 | Brauker et al. |
| 2005/0266582 A1 | 12/2005 | Modlin et al. |
| 2005/0271546 A1 | 12/2005 | Gerber et al. |
| 2005/0274665 A1 | 12/2005 | Heilmann et al. |
| 2005/0282997 A1 | 12/2005 | Ward |
| 2006/0003398 A1 | 1/2006 | Heller et al. |
| 2006/0007391 A1 | 1/2006 | McCabe et al. |
| 2006/0008370 A1 | 1/2006 | Massaro et al. |
| 2006/0015020 A1 | 1/2006 | Neale et al. |
| 2006/0019327 A1 | 1/2006 | Brister et al. |
| 2006/0020186 A1 | 1/2006 | Brister et al. |
| 2006/0036140 A1 | 2/2006 | Brister et al. |
| 2006/0036143 A1 | 2/2006 | Brister et al. |
| 2006/0047095 A1 | 3/2006 | Pacetti |
| 2006/0058868 A1 | 3/2006 | Gale et al. |
| 2006/0065527 A1 | 3/2006 | Samproni |
| 2006/0067908 A1 | 3/2006 | Ding |
| 2006/0068208 A1 | 3/2006 | Tapsak et al. |
| 2006/0078908 A1 | 4/2006 | Pitner et al. |
| 2006/0079740 A1 | 4/2006 | Silver et al. |
| 2006/0086624 A1 | 4/2006 | Tapsak et al. |
| 2006/0134165 A1 | 6/2006 | Pacetti |
| 2006/0142524 A1 | 6/2006 | Lai et al. |
| 2006/0142525 A1 | 6/2006 | Lai et al. |
| 2006/0142526 A1 | 6/2006 | Lai et al. |
| 2006/0142651 A1 | 6/2006 | Brister et al. |
| 2006/0148985 A1 | 7/2006 | Karthauser |
| 2006/0155180 A1 | 7/2006 | Brister et al. |
| 2006/0159718 A1 | 7/2006 | Rathenow et al. |
| 2006/0159981 A1 | 7/2006 | Heller |
| 2006/0171980 A1 | 8/2006 | Helmus et al. |
| 2006/0177379 A1 | 8/2006 | Asgari |
| 2006/0183178 A1 | 8/2006 | Gulati et al. |
| 2006/0183871 A1 | 8/2006 | Ward et al. |
| 2006/0189856 A1 | 8/2006 | Petisce et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200970 A1 | 9/2006 | Brister et al. |
| 2006/0204536 A1 | 9/2006 | Shults et al. |
| 2006/0229512 A1 | 10/2006 | Petisce et al. |
| 2006/0249381 A1 | 11/2006 | Petisce et al. |
| 2006/0249446 A1 | 11/2006 | Yeager |
| 2006/0249447 A1 | 11/2006 | Yeager |
| 2006/0252027 A1 | 11/2006 | Petisce et al. |
| 2006/0253012 A1 | 11/2006 | Petisce et al. |
| 2006/0258761 A1 | 11/2006 | Boock et al. |
| 2006/0258929 A1 | 11/2006 | Goode et al. |
| 2006/0263673 A1 | 11/2006 | Kim et al. |
| 2006/0263839 A1 | 11/2006 | Ward et al. |
| 2006/0269586 A1 | 11/2006 | Pacetti |
| 2006/0275857 A1 | 12/2006 | Kjaer et al. |
| 2006/0275859 A1 | 12/2006 | Kjaer |
| 2006/0289307 A1 | 12/2006 | Yu et al. |
| 2006/0293487 A1 | 12/2006 | Gaymans et al. |
| 2007/0003588 A1 | 1/2007 | Chinn et al. |
| 2007/0007133 A1 | 1/2007 | Mang et al. |
| 2007/0027385 A1 | 2/2007 | Brister et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |
| 2007/0045902 A1 | 3/2007 | Brauker et al. |
| 2007/0059196 A1 | 3/2007 | Brister et al. |
| 2007/0123963 A1 | 5/2007 | Krulevitch |
| 2007/0129524 A1 | 6/2007 | Sunkara |
| 2007/0135698 A1 | 6/2007 | Shah et al. |
| 2007/0142584 A1 | 6/2007 | Schorzman et al. |
| 2007/0155851 A1 | 7/2007 | Alli et al. |
| 2007/0161769 A1 | 7/2007 | Schorzman et al. |
| 2007/0163880 A1 | 7/2007 | Woo et al. |
| 2007/0166343 A1 | 7/2007 | Goerne et al. |
| 2007/0166364 A1 | 7/2007 | Beier et al. |
| 2007/0173709 A1 | 7/2007 | Petisce et al. |
| 2007/0173710 A1 | 7/2007 | Petisce et al. |
| 2007/0197890 A1 | 8/2007 | Boock et al. |
| 2007/0200267 A1 | 8/2007 | Tsai |
| 2007/0202562 A1 | 8/2007 | Curry |
| 2007/0203568 A1 | 8/2007 | Gale et al. |
| 2007/0203573 A1 | 8/2007 | Rudakov et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0229757 A1 | 10/2007 | McCabe et al. |
| 2007/0233013 A1 | 10/2007 | Schoenberg |
| 2007/0235331 A1 | 10/2007 | Simpson et al. |
| 2007/0242215 A1 | 10/2007 | Schorzman et al. |
| 2007/0244379 A1 | 10/2007 | Boock et al. |
| 2007/0275193 A1 | 11/2007 | DeSimone et al. |
| 2007/0299385 A1 | 12/2007 | Santini et al. |
| 2007/0299409 A1 | 12/2007 | Whibourne et al. |
| 2008/0001318 A1 | 1/2008 | Schorzman et al. |
| 2008/0021008 A1 | 1/2008 | Pacetti et al. |
| 2008/0027301 A1 | 1/2008 | Ward et al. |
| 2008/0031918 A1 | 2/2008 | Lawin et al. |
| 2008/0033269 A1 | 2/2008 | Zhang |
| 2008/0034972 A1 | 2/2008 | Gough et al. |
| 2008/0038307 A1 | 2/2008 | Hoffmann |
| 2008/0045824 A1 | 2/2008 | Tapsak et al. |
| 2008/0071027 A1 | 3/2008 | Pacetti |
| 2008/0076897 A1 | 3/2008 | Kunzler et al. |
| 2008/0081184 A1 | 4/2008 | Kubo et al. |
| 2008/0113207 A1 | 5/2008 | Pacetti et al. |
| 2008/0138497 A1 | 6/2008 | Pacetti et al. |
| 2008/0138498 A1 | 6/2008 | Pacetti et al. |
| 2008/0143014 A1 | 6/2008 | Tang |
| 2008/0154101 A1 | 6/2008 | Jain et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0210557 A1 | 9/2008 | Heller et al. |
| 2008/0213460 A1 | 9/2008 | Benter et al. |
| 2008/0305009 A1 | 12/2008 | Gamsey et al. |
| 2008/0305506 A1 | 12/2008 | Suri |
| 2008/0312397 A1 | 12/2008 | Lai et al. |
| 2009/0004243 A1 | 1/2009 | Pacetti et al. |
| 2009/0012205 A1 | 1/2009 | Nakada et al. |
| 2009/0018418 A1 | 1/2009 | Markle et al. |
| 2009/0018426 A1 | 1/2009 | Markle et al. |
| 2009/0030294 A1 | 1/2009 | Petisce et al. |

(56) References Cited

U.S. PATENT DOCUMENTS

| | | |
|---|---|---|
| 2009/0045055 A1 | 2/2009 | Rhodes et al. |
| 2009/0061528 A1 | 3/2009 | Suri |
| 2009/0081803 A1 | 3/2009 | Gamsey et al. |
| 2009/0177143 A1 | 7/2009 | Markle et al. |
| 2009/0247855 A1 | 10/2009 | Boock et al. |
| 2009/0247856 A1 | 10/2009 | Boock et al. |
| 2009/0264719 A1 | 10/2009 | Markle et al. |
| 2009/0287073 A1 | 11/2009 | Boock et al. |
| 2009/0287074 A1 | 11/2009 | Shults et al. |
| 2010/0076283 A1 | 3/2010 | Simpson et al. |
| 2010/0096259 A1 | 4/2010 | Zhang et al. |
| 2010/0119693 A1 | 5/2010 | Tapsak et al. |
| 2010/0145172 A1 | 6/2010 | Petisce et al. |
| 2010/0280347 A1 | 11/2010 | Shah et al. |
| 2011/0147300 A1 | 6/2011 | Xiao et al. |
| 2011/0275919 A1 | 11/2011 | Petisce et al. |
| 2015/0057514 A1 | 2/2015 | Petisce et al. |

FOREIGN PATENT DOCUMENTS

| | | |
|---|---|---|
| EP | 0 286 118 | 10/1988 |
| EP | 0 291 130 | 11/1988 |
| EP | 0 313 951 | 5/1989 |
| EP | 0 320 109 | 6/1989 |
| EP | 0 353 328 | 2/1990 |
| EP | 0 362 145 | 4/1990 |
| EP | 0 390 390 | 10/1990 |
| EP | 0 396 788 | 11/1990 |
| EP | 0 535 898 | 4/1993 |
| EP | 0 563 795 | 10/1993 |
| EP | 0 817 809 | 1/1998 |
| EP | 0 862 648 | 9/1998 |
| GB | 2149918 | 6/1985 |
| GB | 2209836 | 5/1989 |
| JP | 59209609 | 11/1948 |
| JP | 57156004 | 9/1982 |
| JP | 57156005 | 9/1982 |
| JP | 58163402 | 9/1983 |
| JP | 58163403 | 9/1983 |
| JP | 59029693 | 2/1984 |
| JP | 59049803 | 3/1984 |
| JP | 59049805 | 3/1984 |
| JP | 59059221 | 4/1984 |
| JP | 59087004 | 5/1984 |
| JP | 59209608 | 11/1984 |
| JP | 59209610 | 11/1984 |
| JP | 59211459 | 11/1984 |
| JP | 60245623 | 12/1985 |
| JP | 91238319 | 10/1986 |
| JP | 62074406 | 4/1987 |
| JP | 62102815 | 5/1987 |
| JP | 62227423 | 10/1987 |
| JP | 63130661 | 6/1988 |
| JP | 01018404 | 1/1989 |
| JP | 01018405 | 1/1989 |
| JP | 05279447 | 10/1993 |
| JP | 07-083871 | 3/1995 |
| JP | 8196626 | 8/1996 |
| JP | 2002-055076 A | 2/2002 |
| JP | 2002-513602 | 5/2002 |
| WO | WO 1989-002720 | 4/1989 |
| WO | WO 1990-007575 | 7/1990 |
| WO | WO 1992-013271 | 8/1992 |
| WO | WO 1993-014185 | 7/1993 |
| WO | WO 1993-014693 | 8/1993 |
| WO | WO 1993-019701 | 10/1993 |
| WO | WO 1993-023744 | 11/1993 |
| WO | WO 1994-008236 | 4/1994 |
| WO | WO 1996-001611 | 1/1996 |
| WO | WO 1996-025089 | 8/1996 |
| WO | WO 1996-030431 | 10/1996 |
| WO | WO 1996-032076 | 10/1996 |
| WO | WO 1996-036296 | 11/1996 |
| WO | WO 1997-001986 | 1/1997 |
| WO | WO 1997-011067 | 3/1997 |
| WO | WO 1998-030891 | 7/1998 |
| WO | WO 1998-038906 | 9/1998 |
| WO | WO 1999-056613 | 4/1999 |
| WO | WO 2000-059373 | 10/2000 |
| WO | WO 2000-074753 | 12/2000 |
| WO | WO 2001-020019 | 3/2001 |
| WO | WO 2002-053764 | 7/2002 |
| WO | WO 2002-089666 | 11/2002 |
| WO | WO 2003-011131 | 2/2003 |
| WO | WO 2005-044088 | 5/2005 |
| WO | WO 2005-045394 | 5/2005 |
| WO | WO 2006-018425 | 2/2006 |
| WO | WO 2007-114943 | 10/2007 |

OTHER PUBLICATIONS

Abe et al. 1992. Characterization of glucose microsensors for intracellular measurements, Analytical Chemistry 64(18):2160-2163.

Abel et al. 1984. Experience with an implantable glucose sensor as a prerequisite of an artificial beta cell. Biomed. Biochim. Acta 43(5):577-584.

Abel et al. 2002. Biosensors for in vivo glucose measurement: can we cross the experimental stage. Biosensors & Bioelectronics 17:1059-1070.

Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers.com Nov. 7, 2006 http:--www. Answers.com-topic-xenogenic.

Armour et al. Dec. 1990. Application of Chronic Intravascular Blood Glucose Sensor in Dogs. Diabetes 39:1519-1526.

Asberg et al. 2003. Hydrogels of a Conducting Conjugated Polymer as 3-D Enzyme Electrode. Biosensors Bioelectronics 19:199-207.

Atanasov et al. 1994. Biosensor for continuous glucose monitoring. Biotechnology and Bioengineering 43:262-266.

Atanasov et al. 1997. Implantation of a refillable glucose monitoring-telemetry device. Biosensors & Bioelectronics 12:669-680.

Aussedat et al. 1997. A user-friendly method for calibrating a subcutaneous glucose sensor-based hypoglycaemic alarm. Biosensors & Bioelectronics 12( 11):1061-1071.

Bailey et al. 2007. Reduction in hemoglobin A1c with real-time continuous glucose monitoring: results from a 12-week observational study. Diabetes Technology & Therapeutics 9(3):203-210.

Beach et al. 1999. Subminiature implantable potentiostat and modified commercial telemetry device for remote glucose monitoring. IEEE Transactions on Instrumentation and Measurement 48(6):1239-1245.

Bellucci et al. Jan. 1986. Electrochemical behaviour of graphite-epoxy composite materials (GECM) in aqueous salt solutions. Journal of Applied Electrochemistry 16( 1):15-22.

Bessman et al. 1973. Progress toward a glucose sensor for the artificial pancreas. Proceedings of a Workshop on Ion-Selective Microelectrodes, Jun. 4-5, 1973, Boston, MA, 189-197.

Biermann et al. 2008. How would patients behave if they were continually informed of their blood glucose levels? A simulation study using a "virtual" patient. Diabetes Technology & Therapeutics 10:178-187.

Bindra et al. 1989. Pulsed amperometric detection of glucose in biological fluids at a surface-modified gold electrode. Analytical Chemistry 61:2566-2570.

Bindra et al. 1991. Design and In Vitro Studies of a Needle-Type Glucose Sensor for Subcutaneous Monitoring. Analytical Chemistry 63:1692-1696.

Bisenberger et al. 1995. A triple-step potential waveform at enzyme multisensors with thick-film gold electrodes for detection of glucose and sucrose. Sensors and Actuators B 28:181-189.

(56) References Cited

OTHER PUBLICATIONS

Bland et al. 1990. A note on the use of the intraclass correlation coefficient in the evaluation of agreement between two methods of measurement. Comput. Biol. Med. 20(5):337-340.
Bobbioni-Harsch et al. 1993. Lifespan of subcutaneous glucose sensors and their performances during dynamic glycaemia changes in rats. J. Biomed. Eng. 15:457-463.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics 2(Suppl 1):S43-S48.
Bode, B. W. 2000. Clinical utility of the continuous glucose monitoring system. Diabetes Technology & Therapeutics 2(Suppl 1):S35-S41.
Boedeker Plastics, Inc. 2009. Polyethylene Specifications Data Sheet, http:--www.boedeker.com-polye_p.htm [Aug. 19, 2009 3:36:33 PM].
Boland et al. 2001. Limitations of conventional methods of self-monitoring of blood glucose. Diabetes Care 24(11):1858-1862.
Bott, A. W. 1997. A Comparison of Cyclic Voltammetry and Cyclic Staircase Voltammetry. Current Separations 16(1):23-26.
Bowman et al. 1986. The packaging of implantable integrated sensors. IEEE Trans Biomed Eng BME33(2):248-255.
Brauker et al. 1995. Neovascularization of synthetic membranes directed by membrane Microarchitecture. J. Biomed Mater Res 29:1517-1524.
Brauker et al. 1998. Sustained expression of high levels of human factor IX from human cells implanted within an immunoisolation device into athymic rodents. Hum Gene Ther 9:879-888.
Brauker et al. 2001. Unraveling Mysteries at the Biointerface: Molecular Mediator of Inhibition of Blood vessel Formation in the Foreign Body Capsule Revealed. Surfacts Biomaterials 6. 1;5.
Brauker et al. Jun. 27, 1996. Local Inflammatory Response Around Diffusion Chambers Containing Xenografts. Transplantation 61(12):1671-1677.
Braunwald, 2008. Biomarkers in heart failure. N. Engl. J. Med. 358: 2148-2159.
Bremer et al. 2001. Benchmark data from the literature for evaluation of new glucose sensing technologies. Diabetes Technology & Therapeutics 3(3):409-418.
Brooks et al. 1987-88. Development of an on-line glucose sensor for fermentation monitoring. Biosensors 3:45-56.
Bruckel et al. 1989. I n vivo measurement of subcutaneous glucose concentrations with an enzymatic glucose sensor and a wick method. Klin Wochenschr 67:491-495.
Brunner et al. 1998. Validation of home blood glucose meters with respect to clinical and analytical approaches. Diabetes Care 21(4):585-590.
Cai et al. 2004. A wireless, remote query glucose biosensor based on a pH-sensitive polymer. Analytical Chemistry 76(4):4038-4043.
Campanella et al. 1993. Biosensor for direct determination of glucose and lactate in undiluted biological fluids. Biosensors & Bioelectronics 8:307-314.
Candas et al. 1994. An adaptive plasma glucose controller based on a nonlinear insulin-glucose model. IEEE Transactions on Biomedical Engineering 41(2):116-124.
Cass et al. 1984. Ferrocene-mediated enzyme electrodes for amperometric determination of glucose. Analytical Chemistry 36:667-71.
Cassidy et al., Apr. 1993. Novel electrochemical device for the detection of cholesterol or glucose. Analyst, 118:415-418.
Cellulose Acetate Product Description, Apr. 7, 2005, Product No. 419028, Sigma-Aldrich Corp., St. Louis, MO.
Chase et al. 2001. Continuous subcutaneous glucose monitoring in children with type 1 diabetes. Pediatrics 107:222-226.
Chatterjee et al. 1997. Poly(ether Urethane) and poly(ether urethane urea) membranes with high H2S-CH4 selectivity. Journal of Membrane Science 135:99-106.

Chen et al. 2006. A noninterference polypyrrole glucose biosensor. Biosensors and Bioelectronics 22:639-643.
Ciba® Irgacure® 2959 Photoinitiator, Product Description. Apr. 2, 1998. Ciba Specialty Chemicals Inc., Basel, Switzerland. 3 pages.
Claremont et al. 1986. Subcutaneous implantation of a ferrocene-mediated glucose sensor in pigs. Diabetologia 29:817-821.
Claremont et al. Jul. 1986. Potentially-implantable, ferrocene-mediated glucose sensor. J. Biomed. Eng. 8: 272-274.
Clark et al. 1981. One-minute electrochemical enzymic assay for cholesterol in biological materials. Clinical Chemistry 27(12):1978-1982.
Clark et al. 1987. Configurational cyclic voltammetry: increasing the specificity and reliability of implanted electrodes. IEEE-Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
CLSI. 2008. Performance metrics far continuous interstitial glucose monitoring; approved guideline, CLSI document POCT05-A. Wayne, PA: Clinical and Laboratory Standards Institute. 28(33) [72 pages].
Colangelo et al. 1967. Corresion rate measurements in vivo. Journal of Biomedical Materials Research 1:405-414.
Colowick et al. 1976. Methods in Enzymology, vol. XLIV, Immobilized Enzymes. New York: Academic Press [11 pages].
Cox et al. 1985. Accuracy of perceiving blood glucose in IDDM. Diabetes Care 8(6):529-536.
Csoregi et al. 1994. Design, characterization, and one-point in vivo calibration of a subcutaneously implanted glucose electrode. Analytical Chemistry. 66(19):3131-3138.
Dai et al. 1999. Hydrogel Membranes with Mesh Size Asymmetry Based on the Gradient Crosslink of Poly(vinyl alcohol). Journal of Membrane Science 156:67-79.
Danielsson et al. 1988. Enzyme thermistors. Methods in Enzymology 137:181-197.
D'Arrigo et al. 2003. Porous-Si based bioreactors for glucose monitoring and drugs production. Proc. of SPIE 4982: 178-184.
Dassau et al. 2009. In silico evaluation platform for artificial pancreatic ß-cell development-a dynamic simulator for closed loop control with hardware-in-the-loop. Diabetes Technology & Therapeutics 11(3):1-8.
Davies, et al. 1992. Polymer membranes in clinical sensor applications. I. An overview of membrane function. Biomaterials 13(14):971-978.
Davis et al. 1983. Bioelectrochemical fuel cell and sensor based on a quinoprotein, alcohol dehydrogenase. Enzyme Microb. Technology 5:383-388.
Direct 30-30® Blood Glucose Sensor, (Markwell Medical) Catalog, © 1990, ELCO Diagnostics Company [1 page].
Dixon et al. 2002. Characterization in vitro and in vivo of the oxygen dependence of an enzyme-polymer biosensor for monitoring brain glucose. Journal of Neuroscience Methods 119:135-142.
DuPont[1] Dimension AR®. 1998. The chemistry analyzer that makes the most of your time, money and effort. Catalog. Dade International, Chemistry Systems. Newark, DE. 18 pages.
Durliat et al. 1976. Spectrophotometric and electrochemical determinations of L(+)-lactate in blood by use of lactate dehydrogenase from yeast. Clinical Chemistry 22(11):1802-1805.
Edwards Lifesciences. 2002. Accuracy for you and your patients. Marketing materials, 4 pages.
El Degheidy et al. 1986. Optimization of an implantable coated wire glucose sensor. J. Biomed Eng. 8: 121-129.
El-Khatib et al. 2007. Adaptive closed-loop control provides blood-glucose regulation using dual subcutaneous insulin and glucagon infusion in diabetic swine. Journal of Diabetes Science and Technology 1(2):181-192.
El-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Anal. Bioanalytical Chemistry 373:758-761.

(56) References Cited

OTHER PUBLICATIONS

Fahy et al. Mar. 2008. An analysis: hyperglycemic intensive care patients need continuous glucose monitoring—easier said than done. Journal of Diabetes Science and Technology 2(2):201-204.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technology & Therapeutics 5(5):769-779.
Fischer et al. 1987. Assessment of subcutaneous glucose concentration: validation of the wick technique as a reference for implanted electrochemical sensors in normal and diabetic dogs. Diabetologia 30:940-945.
Fischer et al. 1989. Oxygen Tension at the Subcutaneous Implantation Site of Glucose Sensors. Biomed. Biochem 11-12:965-972.
Fischer et al. 1995. Abstract: Hypoglycaemia-warning by means of subcutaneous electrochemical glucose sensors: an animal study. Horm. Metab. Res. 27:53.
Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diabetes Technology & Therapeutics 10:188-193.
Ganesan et al., 2005. Gold layer-based dual crosslinking procedure of glucose oxidase with ferrocene monocarboxylic acid provides a stable biosensor. Analytical Biochemistry 343:188-191.
Ganesh et al. Mar. 2008. Evaluation of the VIA® blood chemistry monitor for glucose in healthy and diabetic volunteers. Journal of Diabetes Science and Technology 2(2): 182-193.
Gao et al. 1989. Determination of Interfacial parameters of cellulose acetate membrane materials by HPLC. J. Liquid Chromatography 12(11):2083-2092.
Garg et al. 2004. Improved Glucose Excursions Using an Implantable Real-Time continuous Glucose Sensor in Adults with Type I Diabetes. Diabetes Care 27:734-738.
Geller et al. 1997. Use of an immunoisolation device for cell transplantation and tumor immunotherapy. Ann NY Acad Sci 831:438-451.
Gerritsen et al. 1999. Performance of subcutaneously implanted glucose sensors for continuous monitoring. The Netherlands Journal of Medicine 54:167-179.
Gerritsen, et al. 2001. Influence of inflammatory cells and serum on the performance of implantable glucose sensors. J Biomed Mater Res 54:69-75.
Gerritsen, M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004. Feasibility of continuous long-term glucose monitoring from a subcutaneous glucose sensor in humans. Diabetes Technology & Therapeutics 6:378-386.
Godsland et al. 2001. Maximizing the Success Rate of Minimal Model Insulin Sensitivity Measurement in Humans: The Importance of Basal Glucose Levels. The Biochemical Society and the Medical Research Society, 1-9.
Gouda et al., Jul. 4, 2003. Thermal inactivation of glucose oxidase. The Journal of Biological Chemistry 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gregg et al. 1990. Cross-Linked Redox Gels Containing Glucose Oxidase for Amperometric Biosensor Applications. Analytical Chemistry 62:258-263.
Gross et al. 2000. Efficacy and reliability of the continuous glucose monitoring system. Diabetes Technology & Therapeutics 2(Suppl 1): S19-S26.
Gross et al. 2000. Performance evaluation of the MiniMed® continuous glucose monitoring system during patient home use. Diabetes Technology & Therapeutics 2(1):49-56.
Guerci et al., 2003. Clinical performance of CGMS in type 1 diabetic patients treated by continuous subcutaneous insulin infusion using insulin analogs. Diabetes Care 26:582-589.
Guo et al., 1998. Modification of cellulose acetate ultrafiltration membrane by gamma ray radiation. Shuichuli Jishi Bianji Weiyuanhui 23(6):315-318 (Abstract only).
Hall et al. 1998. Electrochemical oxidation of hydrogen peroxide at platinum electrodes. Part I: An adsorption-controlled mechanism. Electrochimica Acta 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta 44:2455-2462.
Hall et al. 1999. Electrochemical oxidation of hydrogen peroxide at platinum electrodes. Part IV: Phosphate buffer dependence. Electrochimica Acta 44:4573-4582.
Hall et al. 2000. Electrochemical oxidation of hydrogen peroxide at platinum electrodes. Part V: Inhibition by chloride. Electrochimica Acta 45:3573-3579.
Hamilton Syringe Selection Guide. 2006. Syringe Selection, www.hamiltoncompany.com.
Harrison et al. 1988. Characterization of perfluorosulfonic acid polymer coated enzyme electrodes and a miniaturized integrated potentiostat for glucose analysis in whole blood. Analytical Chemistry 60:2002-2007.
Hashiguchi et al. 1994. Development of a miniaturized glucose monitoring system by combining a needle-type glucose sensor with microdialysis sampling method: Long-term subcutaneous tissue glucose monitoring in ambulatory diabetic patients. Diabetes Care 17(5):387-396.
Heller, A. 1992. Electrical Connection of Enzyme Redox Centers to Electrodes. J. Phys. Chem. 96:3579-3587.
Heller, A. 1999. Implanted electrochemical glucose sensors for the management of diabetes. Annu Rev Biomed Eng 1:153-175.
Heller, A. 2003. Plugging metal connectors into enzymes. Nature Biotechnology 21:631-632.
Hicks, 1985. In Situ Monitoring. Clinical Chemistry 31(12):1931-1935.
Hitchman, M. L. 1978. Measurement of Dissolved Oxygen. In Elving et al. (Eds.). . New York: John Wiley & Sons. Chemical Analysis, vol. 49, Chap. 3, pp. 34-49, 59-123.
Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Analytical Chemistry 75:3308-3315.
http:--www.merriam-webster.com-dictionary, definition for "aberrant," Aug. 19, 2008, p. 1.
Hu, et al. 1993. A needle-type enzyme based lactate sensor for in vivo monitoring. Analytica Chimica Acta, 281:503-511.
Huang et al. Aug. 1975. Eleotrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Eleotrode. U.S. Department of Commerce-NTIS, pp. 1-116.
Huang et al., Sep. 1997. A 0.5mW Passive Telemetry IC for Biomedical Applications, Proceedings of the 23rd European Solid-State Circuits Conference (ESSCIRC '97), pp. 172-175, Southampton, UK.
Hunter et al. Mar. 31, 2000. Minimally Invasive Glucose Sensor and Insulin Delivery System. MIT Home Automation and Healthcare Consortium. Progress Report No. 2-5 [17 pages].

(56) References Cited

OTHER PUBLICATIONS

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications 12:295-301.
Jaffari et al. 1995. Recent advances in amperometric glucose biosensors for in vivo monitoring. Physiol. Meas. 16: 1-15.
Jensen et al. 1997. Fast wave forms for pulsed electrochemical detection of glucose by incorporation of reductive desorption of oxidation products. Analytical Chemistry 69(9):1776-1781.
Jeutter, D. C. 1982. A transcutaneous implanted battery recharging and biotelemeter power switching system. IEEE Trans Biomed Eng 29:314-321.
Jobst et al. 1996. Thin-Film Microbiosensors for Glucose-Lactate Monitoring. Analytical Chemistry 8(18):3173-3179.
Johnson 1991. Reproducible electrodeposition of biomolecules for the fabrication of miniature electroenzymatic biosensors. Sensors and Actuators B 5:85-89.
Johnson et al. 1992. In vivo evaluation of an electroenzymatic glucose sensor implanted in subcutaneous tissue. Biosensors & Bioelectronics 7:709-714.
Johnson et al. 1997. Abstract: Neovascularization of cell transplantation devices: Role of membrane architecture and encapsulated tissue. Abstracts of Papers, Am. Chem. Soc. 214:2 P 305-PMSE.
Jovanovic et al. 1997. The Thermogravimetric analysis of some polysiloxanes. Polym Degrad Stability 61:87-93.
Jovanovic, L. 2000. The role of continuous glucose monitoring in gestational diabetes mellitus. Diabetes Technology & Therapeutics 2(Suppl 1):S67-S71.
Kacaniklic et al. 1994. Amperometric Biosensors for Detection of L- and D-Amino Acids Based on Coimmoblized Peroxidase and L- and D-Amino Acid Oxidases in Carbon Paste Electrodes. Electroanalysis 6(5-6): 381-390.
Kamath et al. Nov. 13-15, 2008. Calibration of a continuous glucose monitor: effect of glucose rate of change. Eighth Annual Diabetes Technology Meeting, p. A88.
Kang et al. 2003. In vitro and short-term in vivo characteristics of a Kel-F thin film modified glucose sensor. Anal Sci 19:1481-1486.
Kargol et al. 2001. Studies on the structural properties of porous membranes: measurement of linear dimensions of solutes. Biophys Chem 91:263-271.
Karube et al. 1993. Microbiosensors for acetylcholine and glucose. Biosensors & Bioelectronics 8:219-228.
Kaufman et al. 2001. A pilot study of the continuous glucose monitoring system. Diabetes Care 24(12):2030-2034.
Kaufman. 2000. Role of the continuous glucose monitoring system in pediatric patients. Diabetes Technology & Therapeutics 2(Suppl. 1):S-49-S52.
Kawagoe et al. 1991. Enzyme-modified organic conducting salt microelectrode. Analytical Chemistry 63:2961-2965.
Keedy et al. 1991. Determination of urate in undiluted whole blood by enzyme electrode. Biosensors & Bioelectronics 6: 491-499.
Kerner et al. 1988. A potentiaiiy implantable enzyme electrode for amperometric measurement of glucose. Horm Metab Res Suppl. 20:8-13.
Kerner et al. 1993. The function of a hydrogen peroxide-detecting electroenzymatic glucose electrode is markedly impaired in human sub-cutaneous tissue and plasma. Biosensors & Bioelectronics 8:473-482.
Kiechle, F.L. 2001. The impact of continuous glucose monitoring on hospital point-of-care testing programs. Diabetes Technology & Therapeutics 3:647-649.
Klueh et al. 2003. Use of Vascular Endothelial Cell Growth Factor Gene Transfer to Enhance Implantable Sensor Function in Vivo. J. Biomed Materials Res 67A:1072-1086.
Klueh et al. 2007. Inflammation and glucose sensors: use of dexamethasone to extend glucose sensor function and life span in vivo. Journal of Diabetes Science and Technology 1(4):496-504.
Kondo et al. 1982. A miniature glucose sensor, implantable in the blood stream. Diabetes Care. 5(3):218-221.
Koschinsky et al. 1988. New approach to technical and clinical evaluation of devices for self-monitoring of blood glucose. Diabetes Care 11(8): 619-619.
Koschinsky et al. 2001. Sensors for glucose monitoring: Technical and clinical aspects. Diabetes Metab. Res. Rev. 17:113-123.
Kost et al. 1985. Glucose-sensitive membranes containing glucose oxidase: activity, swelling, and permeability studies. Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. B iosensors & Bioelectronics 6:31-36.
Kraver et al. 2001. A mixed-signal sensor interface microinstrument. Sensors and Actuators A 91:266-277.
Kruger et al. 2000. Psychological motivation and patient education: A role for continuous glucose monitoring. Diabetes Technology & Therapeutics 2(Suppl 1):S93-S97.
Kulys et al., 1994. Carbon-paste biosensors array for long-term glucose measurement. Biosensors & Bioelectronics 9:491-500.
Kunjan et al. Mar. 2008. Automated blood sampling and glucose sensing in critical care settings. Journal of Diabetes Science and Technology 2(3):194-200.
Kunzler et al. 1993. Hydrogels based on hydrophilic side chain siloxanes. Poly Mat Sci and Eng 69:226-227.
Kunzler et al. Aug. 21, 1995. Contact lens materials. Chemistry & Industry, Aug. 21, 1995, pp. 651-655.
Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310.
Kusano, H. 1989. Glucose enzyme electrode with percutaneous interface which operates independently of dissolved oxygen. Clin Phys Physiol Meas. 10(1):1-9.
Ladd et al. 1996. Structure Determination by X-ray Crystallography, 3rd ed. Plenum, 1996. Ch. 1, pp. xxi-xxiv and 1-58.
Lee et al. 1999. Effects of pore size, void volume, and pore connectivity on tissue responses. Society for Biomaterials 25th Annual Meeting, p. 171.
Lehmann et al. May 1994. Retrospective validation of a physiological model of glucose-insulin interaction in type 1 diabetes mellitus. Med. Eng. Phys. 16:193-202.
Lerner et al. 1984. An implantable electrochemical glucose sensor. Ann. N. Y. Acad. Sci. 428:263-278.
Lewandowski et al. 1988. Evaluation of a miniature blood glucose sensor. Trans Am Soc Artif Intern Organs 34:255-258.
Leypoldt et al. 1984. Model of a two-substrate enzyme electrode for glucose. Analytical Chemistry 56:2896-2904.
Linke et al. 1994. Amperometric biosensor for in vivo glucose sensing based on glucose oxidase immobilized in a redox hydrogel. Biosensors & Bioelectronics 9:151-158.
Loffler et al. 1995. Separation and determination of traces of ammonia in air by means of chromatomembrane cells. Fresenius J Analytical Chemistry 352:613-614.
Lowe, 1984. Biosensors. Trends in Biotechnology 2(3):59-65.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2): 132-139.
Lyandres et al. 2008. Progress toward an in vivo surface-enhanced raman spectroscopy glucose sensor. Diabetes Technology & Therapeutics 10(4):257-265.
Lyman D. 1960. Polyurethanes. I. The Solution Polymerization of Diisocyanates with Ethylene Glycol. J. Polymer Sci XLV:45-49.
Madaras et al. 1996. Microfabricated amperometric creatine and creatinine biosensors. Analytica Chimica Acta 319:335-345.

(56) References Cited

OTHER PUBLICATIONS

Maidan et al. 1992. Elimination of Electrooxidizable Interferent-Produced Currents in Amperometric Biosensors. Analytical Chemistry 64:2889-2896.
Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy. Clinical Chemistry 45(9):1651-1658.
Maran et al. 2002. Continuous subcutaneous glucose monitoring in diabetic patients: A multicenter analysis. Diabetes Care 25(2):347-352.
March, W. F. 2002. Dealing with the delay. Diabetes Technology & Therapeutics 4(1):49-50.
Marena et al. 1993. The artificial endocrine pancreas in clinical practice and research. Panminerva Medica 35(2): 67-74.
Mascini et al. 1989. Glucose electrochemical probe with extended linearity for whole blood. J Pharm Biomed Anal 7(12):1507-1512.
Mastrototaro et al. 1991. An electroenzymatic glucose sensor fabricated on a flexible substrate. Sensors and Actuators B 5:139-144.
Mastrototaro et al. 2003. Reproducibility of the continuous glucose monitoring system matches previous reports and the intended use of the product. Diabetes Care 26:256; author reply p. 257.
Mastrototaro, J. J. 2000. The MiniMed continuous glucose monitoring system. Diabetes Technology & Therapeutics 2(Suppl 1 ):S13-S18.
Matsumoto et al. 1998. A micro-planar amperometric glucose sensor unsusceptible to interference species. Sensors and Actuators B 49:68-72.
Matsumoto et al. 2001. A long-term lifetime amperometric glucose sensor with a perfluorocarbon polymer coating. Biosensors & Bioelectronics 16:271-276.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diabetes Technology & Therapeutics 10:149-159.
McCartney et al. 2001. Near-infrared fluorescence lifetime assay for serum glucose based on allophycocyanin-labeled concanavalin A. Anal Biochem 292:216-221.
McGrath et al. 1995. The use of differential measurements with a glucose biosensor for interference compensation during glucose determinations by flow injection analysis. Biosensors & Bioelectronics 10:937-943.
McKean et al. Jul. 7, 1988. A Telemetry Instrumentation System for Chronically Implanted Glucose and Oxygen Sensors. IEEE Transactions on Biomedical Engineering BME 35:526-532.
Memoli et al. 2002. A comparison between different immobilised glucoseoxidase-based electrodes. J Pharm Biomed Anal 29:1045-1052.
Merriam-Webster Online Dictionary. Jan. 11, 2010. Definition of "acceleration". http:--www.merriam- webster.com-dictionary-Acceleration.
Merriam-Webster Online Dictionary. Jan. 11, 2010. Definition of "system". http:--www.merriam-webster.com-dictionary-System.
Merriam-Webster Online Dictionary, Apr. 23, 2007. Definition of "nominal". http:--www.merriam-webster.com-dictionary-nominal.
Meyerhoff et al. 1992. On line continuous monitoring of subcutaneous tissue glucose in men by combining portable glucosensor with microdialysis. Diabetologia 35:1087-1092.
Miller et al. 1989. Generation of IL1-like activity in response to biomedical polymer implants: a comparison of in vitro and in vivo models. J Biomed Mater Res 23:1007-1026.
Miller et al. 1989. In vitro stimulation of fibroblast activity by factors generated from human monocytes activated by biomedical polymers. Journal of J Biomed Mater Res 23:911-930.
Miller, A. 1988. Human monocyte-macrophage activation and interleukin 1 generation by biomedical polymers. J Biomed Mater Res 23:713-731.
Moatti-Sirat et al. 1992. Evaluating in vitro and in vivo the interference of ascorbate and acetaminophen on glucose detection by a needle-type glucose sensor. Biosensors & Bioelectronics 7:345-352.
Moatti-Sirat et al. 1992. Towards continuous glucose monitoring: in vivo evaluation of a miniaturized glucose sensor implanted for several days in rat subcutaneous tissue. Diabetologia 35:224-230.
Moatti-Sirat et al. Jun. 1994. Reduction of acetaminophen interference in glucose sensors by a composite Nafion membrane: demonstration in rats and man. Diabetologia 37(6):610-616.
Morff et al. 1990. Microfabrication of reproducible, economical, electroenzymatic glucose sensors, Annual International Conference of the IEEE Engineering in Medicine and Biology Society 12(2):0483-0484.
Mosbach et al. 1975. Determination of heat changes in the proximity of immobilized enzymes with an enzyme thermistor and its use for the assay of metabolites. Biochim. Biophys. Acta 403:256-265.
Motonaka et al. 1993. Determination of cholesterol and cholesterol ester with novel enzyme microsensors. Analytical Chemistry 65:3258-3261.
Moussy et al. 1993. Performance of subcutaneously implanted needle-type glucose sensors employing a novel trilayer coating. Analytical Chemistry 85: 2072-2077.
Moussy et al. 2000. Biomaterials community examines biosensor biocompatibility. Diabetes Technology & Therapeutics 2:473-477.
Moussy, Francis, 2002. Implantable Glucose Sensor: Progress and Problems. Sensors 1:270-273.
Mowery et al. 2000. Preparation and characterization of hydrophobic polymeric films that are thromboresistant via nitric oxide release. Biomaterials 21:9-21.
Murphy, et al. 1992. Polymer membranes in clinical sensor applications. II. The design and fabrication of permselective hydrogels for electrochemical devices. Biomaterial, 13( 14):979-990.
Muslu. 1991. Trickling filter performance. Applied Biochem. Biotech. 37:211-224.
Myler et al. 2002. Ultra-thin-polysiloxane-film-composite membranes for the optimisation of amperometric oxidase enzyme electrodes. Biosensors & Bioelectronics 17:35-43.
Nafion® Solution Product Description, Product No. 70160, Sigma-Aldrich Corp., St. Louis, MO. Downloaded from https:--www.signaaldrich.com-cgi-bin-hsrun-Suite7-Suite-HAHTpage-Suite.HsExternal Prod . . . on Apr. 7, 2005.
Nakayama et al. 1992. Surface fixation of hydrogels: heparin and glucose oxidase hydrogelated surfaces. ASAIO Journal 38:M421-M424.
Nam et al. 2000. A novel fabrication method of macroporous biodegradable polymer scaffolds using gas foaming salt as a porogen additive. J Biomed Mater Res 53:1-7.
Ohara et al. 1994. "Wired" enzyme electrodes for amperometric determination of glucose or lactate in the presence of interfering substances. Analytical Chemistry 66:2451-2457.
Ohara, et al. Dec. 1993. Glucose electrodes based on cross-linked bis(2,2'-bipyridine)chloroosmium(+-2+) complexed poly(I-vinylimidazole) films. Analytical Chemistry 65:3512-3517.
Okuda et al. 1971. Mutarotase effect on micro determinations of D-glucose and its anomers with (3-D-glucose oxidase. Anal Biochem 43:312-315.
Oxford English Dictionary Online. Jan. 11, 2010. Definition of "impending". http:--www.askoxford.com-results-?view=dev dict &field-12668446 Impending&branch=.
Palmisano et al. 2000. Simultaneous monitoring of glucose and lactate by an interference and crosstalk free dual electrode amperometric biosensor based on electropolymerized thin films. Biosensors & Bioelectronics 15:531-539.
Panetti 2002. Differential effects of sphingosine 1-phosphate and lysophosphatidic acid on endothelial cells. Biochimica et Biophysica Acta 1582:190-196.

(56) References Cited

OTHER PUBLICATIONS

Park et al. 2002. Gas separation properties of polysiloxane-polyether mixed soft segment urethane urea membranes. J. Membrane Science 204:257-269.
Patel et al. 2003. Amperometric glucose sensors based on ferrocene containing polymeric electron transfer systems—a preliminary report. Biosensors & Bioelectronics 18:1073-6.
Peacock et al. 2008. Cardiac troponin and outcome in acute heart failure. N. Engl. J. Med. 358: 2117-2126.
Pegoraro et al. 1995. Gas transport properties of siloxane polyurethanes. Journal of Applied Polymer Science 57:421-429.
Pfeiffer et al. 1992. On line continuous monitoring of subcutaneous tissue glucose is feasible by combining portable glucosensor with microdialysis. Horm. Metab. Res. 25:121-124.
Pfeiffer, E.F. 1990. The glucose sensor: the missing link in diabetes therapy. Horm Metab Res Suppl. 24:154-164.
Phillips and Smith. 1988. Bromedical Applications of Polyurethanes: Implications of Failure Mechanisms. J. Biomat. Appl. 3:202-227.
Pichert et al. 2000. Issues for the coming age of continuous glucose monitoring. Diabetes Educator 26(6):969-980.
Pickup et al. 1987-88. Implantable glucose sensors: choosing the appropriate sensing strategy. Biosensors 3:335-346.
Pickup et al. 1988. Progress towards in vivo glucose sensing with a ferrocene-mediated amperometric enzyme electrode. pp. 34-36.
Pickup et al. 1989. In vivo molecular sensing in diabetes mellitus: an implantable glucose sensor with direct electron transfer. Diabetologia 32:213-217.
Pickup et al. 1989. Potentially-implantable, amperometric glucose sensors with mediated electron transfer: improving the operating stability. Biosensors 4:109-119.
Pineda et al. 1996. Bone regeneration with resorbable polymeric membranes. III. Effect of poly(L-lactide) membrane pore size on the bone healing process in large defects. J. Biomedical Materials Research 31:385-394.
Pinner et al. 1959. Cross-linking of cellulose acetate by ionizing radiation. Nature 184(4695):1303-1304.
Pishko et al. 1991. Amperometric glucose microelectrodes prepared through immobilization of glucose oxidase in redox hydrogels. Analytical Chemistry 63:2268-2272.
Pitzer et al. 2001. Detection of hypoglycemia with the GlucoWatch biographer. Diabetes Care 24(5):881-885.
Poitout et al. 1991. In Vitro and In Vivo Evaluation in Dogs of a Miniaturized Glucose Sensor. ASAIO Transactions 37:M298-M300.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode. Electrochimica Acta 26(6):725-729.
Quinn et al. 1995. Kinetics of glucose delivery to subcutaneous tissue in rats measured with 0.3-mm amperometric microsensors. Am. J. Physiology 269 (Endocrinol. Metab. 32):E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine. Carbon 29(2):165-171.
Ratner, B.D. 2002. Reducing capsular thickness and enhancing angiogenesis around implant drug release systems. J Control Release 78:211-216.

Reach et al. 1986. A Method for Evaluating in vivo the Functional Characteristics of Glucose Sensors. Biosensors 2:211-220.
Reach et al. 1992. Can continuous glucose monitoring be used for the treatment of diabetes? Analytical Chemistry 64(5):381-386.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. 1989. Automated feedback control of subcutaneous glucose concentration in diabetic dogs. Diabetologia 32:573-76.
Rebrin et al. 1992. Subcutaneous glucose monitoring by means of electrochemical sensors: fiction or reality? J. Biomed. Eng. 14:33-40.
Reusch. 2004. Chemical Reactivity. Organometallic Compounds. Virtual Textbook of Organic Chem. pp. 1-16, http:--www.cem.msu.edu-~reusch-VirtualText-orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assistance improves glycemic control and glucose stability in pump-treated patients. Diabetes Technology & Therapeutics 10(3):194-199.
Rivers et al. 2001. Central venous oxygen saturation monitoring in the critically ill patient. Current Opinion in Critical Care 7:204-211.
Sachlos et al. 2003. Making Tissue Engineering Scaffolds Work. Review on the Application of Sold Freeform Fabrication Technology to the Production of Tissue Engineering Scaffolds. European Cells and Materials 5:29-40.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Sakakida et al. 1993. Ferrocene-Mediated Needle Type Glucose Sensor Covered with Newly Designed Biocompatible Membrane. Sensors and Actuators B 13-14:319-322.
Salardi et al. 2002. The glucose area under the profiles obtained with continuous glucose monitoring system relationships with HbA1c in pediatric type 1 diabetic patients. Diabetes Care 25(10): 1840-1844.
Samuels, M.P. 2004. The effects of flight and altitude. Arch Dis Child. 89: 448-455.
San Diego Plastics, Inc. 2009. Polyethylene Data Sheet, http:--www.sdplastics.com-polyeth.html.
Sanders et al. 2003. Fibrous Encapsulation of Single Polymer Microfibers Depends on their Vertical Dimension in subcutaneous Tissue Polymer Microfibers. J. Biomed Matl Res 67A:1181-1187.
Sansen et al. 1985. Glucose sensor with telemetry system. In Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schmidtke et al. Jan. 1998. Measurement and modeling of the transient difference between blood and subcutaneous glucose concentrations in the rat after injection of insulin. Proc Natl Acad Sci U S A 95: 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990. Development of a potentially wearable glucose sensor for patients with diabetes mellitus: design and in-vitro evaluation. Biosensors & Bioelectronics 5:37-46.
Schuler et al. 1999. Modified gas-permeable silicone rubber membranes for covalent immobilisation of enzymes and their use in biosensor development. Analyst 124:1181-1184.
Selam, J. L. 1997. Management of diabetes with glucose sensors and implantable insulin pumps. From the dream of the 60s to the realities of the 90s. ASAIO J 43:137-142.

(56) References Cited

OTHER PUBLICATIONS

Service et al. 1970. Mean amplitude of glycemic excursions, a measure of diabetic instability. Diabetes 19: 644-655.
Service et al. 1987. Measurements of glucose control. Diabetes Care 10: 225-237.
Service, R. F. 2002. Can sensors make a home in the body? Science 297:962-963.
Sharkawy et al. 1997. Engineering the tissue which encapsulates subcutaneous implants. I. Diffusion properties. J Biomed Mater Res. 37:401-412.
Shaw et al. 1991. In vitro testing of a simply constructed, highly stable glucose sensor suitable for implantation in diabetic patients. Biosensors & Bioelectronics 6:401-406.
Shichiri et al. 1982. Wearable artificial endocrine pancreas with needle-type glucose sensor. Lancet 2:1129-1131.
Shichiri et al. 1985. Needle Type Glucose Sensor for earable Artificial Endocrine Pancreas. In Ko, W. H. (Ed.). Implantable Sensors for Closed Loop Prosthetic Systems. Chap. 15, pp. 197-210, Future Publishing Co., Mount Kisco, NY.
Shichiri et al. 1989. Membrane Design for Extending the Long-Life of an Implantable Glucose Sensor. Diab. Nutr. Metab. 2:309-313.
Shichiri, et al. 1983. Glycaemic Control in Pancreatectomized Dogs with a Wearable Artificial Endocrine Pancreas. Diabetologia 24:179-184.
Shults et al. 1994. A telemetry-instrumentation system for monitoring multiple subcutaneously implanted glucose sensors. IEEE Transactions on Biomedical Engineering BME 41(10):937-942.
Sieminski et al. 2000. Biomaterial-microvasculature interactions. Biomaterials 21:2233-2241.
Skyler, J. S. 2000. The economic burden of diabetes and the benefits of improved glycemic control: The potential role of a continuous glucose monitoring system. Diabetes Technology & Therapeutics 2(Suppl 1):S7-S12.
Slater-Maclean et al. 2008. Accuracy of glycemic measurements in the critically ill. Diabetes Technology & Therapeutics 10:169-177.
Sokol et al. 1980. Immobilized-enzyme rate-determination method for glucose analysis. Clinical Chemistry 26(1):89-92.
Sriyudthsak et al. 1996. Enzyme-epoxy membrane based glucose analyzing system and medical applications. Biosensors & Bioelectronics 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves. Journal of the Electrochemical Society 104(1):56-63.
Sternberg et al. 1988. Study and Development of Multilayer Needle-type Enzyme-based Glucose Microsensors. Biosensors 4:27-40.
Stokes. 1988. Polyether Polyurethanes: Biostable or Not? J. Biomat. Appl. 3:228-259.
Suh et al. 2002. Behavior of fibroblasts on a porous hyaluronic acid incorporated collagen matrix. Yonsei Medical Journal 43(2):193-202.
Sumino T. et al. 1998. Preliminary study of continuous glucose monitoring with a microdialysis technique. Proceedings of the IEEE 20(4):1775-1778.
Takegami et al. 1992. Pervaporation of ethanol water mixtures using novel hydrophobic membranes containing polydimethylsiloxane. Journal of Membrane Science 75: 93-105.
Tanenberg et al. 2000. Continous glucose monitoring system: A new approach to the diagnosis of diabetic gastroparesis. Diabetes Technology & Therapeutics 2(Suppl 1):S73-S80.
Tang et al. 1993. Fibrin(ogen) mediates acute inflammatory responses to biomaterials. J Exp Med 178:2147-2156.
Tang et al. 1995. Inflammatory responses to biomaterials. Am J Clin Pathol 103:466-471.
Tang et al. 1996. Molecular determinants of acute inflammatory responses to biomaterials. J Clin Invest 97:1329-1334.
Tang et al. 1998. Mast cells mediate acute inflammatory responses to implanted biomaterials. Proc Natl Acad Sci U S A 95:8841-8846.
Tatsuma et al. 1991. Oxidase-peroxidase bilayer-modified electrodes as sensors for lactate, pyruvate, cholesterol and uric acid. Analytica Chimica Acta 242:85-89.
Thome et al. 1995. Abstract: Can the decrease in subcutaneous glucose concentration precede the decrease in blood glucose level? Proposition for a push-pull kinetics hypothesis. Horm. Metab. Res. 27:53.
Thome-Duret et al. 1996. Modification of the sensitivity of glucose sensor implanted into subcutaneous tissue. Diabetes Metabolism 22:174-178.
Thome-Duret et al. 1996. Use of a subcutaneous glucose sensor to detect decreases in glucose concentration prior to observation in blood. Analytical Chemistry 68:3822-3826.
Thome-Duret et al. 1998. Continuous glucose monitoring in the free-moving rat. Metabolism, 47:799-803.
Thompson et al. 1986. In Vivo Probes: Problems and Perspectives. Department of Chemistry, University of Toronto, Canada, pp. 255-261.
Tibell et al. 2001. Survival of macroencapsulated allogeneic parathyroid tissue one year after transplantation in nonimmunosuppressed humans. Cell Transplant 10:591-599.
Tierney et al. 2000. Effect of acetaminophen on the accuracy of glucose measurements obtained with the GlucoWatch biographer. Diabetes Technology & Therapeutics 2(2):199-207.
Tierney et al. 2000. The GlucoWatch® biographer: A frequent, automatic and noninvasive glucose monitor. Ann. Med. 32:632-641.
Torjman et al. Mar. 2008. Glucose monitoring in acute care: technologies on the horizon. Journal of Diabetes Science & Technology 2(2):178-181.
Trecroci, D. 2002. A Glimpse into the Future-Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner and Pickup 1985. Diabetes mellitus: biosensors for research and management. Biosensors 1:85-115.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta 163: 161-174.
Turner, A.P.F. 1988. Amperometric biosensor based on mediator-modified electrodes. Methods in Enzymology 137:90-103.
Unger et al. 2004. Glucose control in the hospitalized patient. Emergency Med 36(9):12-18.
Updike et al. 1967. The enzyme electrode. Nature 214:986-988.
Updike et al. 1988. Laboratory Evaluation of New Reusable Blood Glucose Sensor. Diabetes Care 11:801-807.
Updike et al. 1994. Enzymatic glucose sensor: Improved long-term performance in vitro and in vivo. ASAIO Journal 40(2):157-163.
Updike et al. 1997. Principles of long-term fully implanted sensors with emphasis on radiotelemetric monitoring of blood glucose form inside a subcutaneous foreign body capsule (FBC). Fraser, D.M. (Ed.), Biosensors in the Body. New York. John Wiley & Sons Ltd., Chapter 4, pp. 117-137.
Updike et al. 2000. A subcutaneous glucose sensor with improved longevity, dynamic range, and stability of calibration. Diabetes Care 23(2):208-214.
Utah Medical Products Inc., Blood Pressure Transducers product specifications. 6 pp. 2003-2006, 2003.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
von Woedtke et al. 1989. In situ calibration of implanted electrochemical glucose sensors. Biomed Biochim. Acta 48(11-12):943-952.
Wade, L.G., Jr. 1987. Organic Chemistry, Chapter 17, Reactions of Aromatic Compounds pp. 762-763.

(56) References Cited

OTHER PUBLICATIONS

Wagner et al. 1998. Continuous amperometric monitoring of glucose in a brittle diabetic chimpanzee with a miniature subcutaneous electrode. Proc. Natl. Acad. Sci. A 95:6379-6382.
Wang et al. 1994. Highly Selective Membrane-Free, Mediator-Free Glucose Biosensor, Analytical Chemistry 66:3600-3603.
Wang et al. 1997. Improved ruggedness for membrane-based amperometric sensors using a pulsed amperometric method. Analytical Chemistry 69:4482-4489.
Ward et al. 2000. Rise in background current overtime in a subcutaneous glucose sensor in the rabbit: Relevance to calibration and accuracy. Biosensors & Bioelectronics 15:53-61.
Ward et al. 2000. Understanding Spontaneous Output Fluctuations of an Amperometric Glucose Sensor: Effect of Inhalation Anesthesia and use of a Nonenzyme Containing Electrode. ASAIO Journal 46:540-546.
Ward et al. 2002. A new amperometric glucose microsensor: In vitro and short-term in vivo evaluation. Biosensors & Bioelectronics 17:181-189.
Ward et al. 2004. A wire-based dual-analyte sensor for Glucose and Lactate: In Vitro and In Vivo Evaluation. Diabetes Technology & Therapeutics 6(3):389-401.
Wientjes, K. J. C. 2000. Development of a glucose sensor for diabetic patients (Ph.D. Thesis).
Wikipedia 2006. "Intravenous therapy," http:--en.wikipedia.org-wiki-intravenous_therapy, Aug. 15, 2006 [6 pages].
Wiley Electrical and Electronics Engineering Dictionary, 2004. John Wiley & Sons, Inc. pp. 141, 142, 548, 549.
Wilkins et al. 1988. The coated wire electrode glucose sensor. Horm Metab Res Suppl. 20:50-55.
Wilkins et al. 1995. Integrated implantable device for long-term glucose monitoring. Biosensors & Bioelectronics 10:485-494.
Wilkins et al. 1996. Glucose monitoring: state of the art and future possibilities. Med Eng Phys 18:273-288.
Wilson et al. 1992. Progress toward the development of an implantable sensor for glucose. Clin. Chem. 38(9):1613-1617.
Wilson et al. 2000. Enzyme-based biosensors for in vivo measurements. Chem. Rev. 100:2693-2704.
Wood, W. et al. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al. 2008. Measurement of glucose in blood with a phenylboronic acid optical sensor. Journal of Diabetes Science & Technology 2(2):213-220.
Wright et al. 1999. Bioelectrochemical dehalogenations via direct electrochemistry of poly(ethylene oxide)-modified myoglobin. Electrochemistry Communications 1: 603-611.
Wu et al. 1999. In situ electrochemical oxygen generation with an immunoisolation device. Annals New York Academy of Sciences pp. 105-125.
Yamasaki et al. 1989. Direct measurement of whole blood glucose by a needle-type sensor. Clinica Chimica Acta 93:93-98.
Yamasaki, Yoshimitsu, 1984. The development of a needle-type glucose sensor for wearable artificial endocrine pancreas. Medical Journal of Osaka University 35(1-2):25-34.
Yang et al 1996. A glucose biosensor based on an oxygen electrode: In-vitro performances in a model buffer solution and in blood plasma. Biomedical Instrumentation & Technology 30:55-61.
Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate-Nafion Composite Membranes. Journal of Membrane Science 237:145-161.
Ye et al. 1993. High Current Density 'Wired' Quinoprotein Glucose Dehydrogenase Electrode. Analytical Chemistry 65:238-241.
Zamzow et al. 1990. Development and evaluation of a wearable blood glucose monitor. ASAIO Transactions 36(3):M588-M591.
Zethelius et al. 2008. Use of multiple biomarkers to improve the prediction of death from cardiovascular causes. N. Engl. J. Med. 358: 2107-2116.
Zhang et al 1993. Electrochemical oxidation of H202 on Pt and Pt + Ir electrodes in physiological buffer and its applicability to H202-based biosensors. J. Electroanalytical Chemistry 345:253-271.
Zhang et al. 1993. In vitro and in vivo evaluation of oxygen effects on a glucose oxidase based implantable glucose sensor. Analytica Chimica Acta 281:513-520.
Zhang et al. 1994. Elimination of the acetaminophen interference in an implantable glucose sensor. Analytical Chemistry 66(7):1183-1188.
Zhu et al. 1994. Fabrication and characterization of glucose sensors based on a microarray H202 electrode. Biosensors & Bioelectronics 9: 295-300.
Zhu et al. 2002. Planar amperometric glucose sensor based on glucose oxidase immobilized by chitosan film on prussian blue layer. Sensors 2:127-136.
EP 04778806.2, filed Jul. 21, 2004: EPO Extended Search Report dated Dec. 15, 2009.
EP 04778806.2, filed Jul. 21, 2004: EPO Examination Report dated May 18, 2010.
EP 06750217.9, filed Apr. 14, 2006: EPO Search Report dated Oct. 15, 2009.
JP 2006-521208, filed Jul. 21, 2004: JPO Examination Report dated Jun. 1, 2010.
JP 2006-521208, filed Jul. 21, 2004: JPO Notice of Allowance dated Feb. 22, 2011.
PCT/US2002/023903, filed Jul. 26, 2002: International Search Report dated Feb. 27, 2003.
PCT/US2002/023903, filed Jul. 26, 2002; International Preliminary Examination Report dated Apr. 18, 2005.
PCT/US2004/023454, filed Jul. 21, 2004: International Preliminary Report on Patentability dated Feb. 9, 2006.
PCT/US2004/023454, filed Jul. 21, 2004: International Search Report and Written Opinion dated Oct. 19, 2005.
PCT/US2004/035499, filed Oct. 26, 2004: International Preliminary Report on Patentability dated Feb. 9, 2006.
PCT/US2004/038726, filed Nov. 17, 2004: International Preliminary Report on Patentability dated Nov. 7, 2006.
PCT/US2004/038726, filed Nov. 17, 2004: International Search Report and Written Opinion dated Sep. 16, 2006.
PCT/US2007/003881, filed Feb. 14, 2007: International Preliminary Report on Patentability dated Oct. 23, 2008.
PCT/US2007/003881, filed Feb. 14, 2007: International Search Report and Written Opinion dated Jan. 4, 2008.
U.S. Appl. No. 11/410,392, filed Apr. 25, 2006: Partial electronic file history through Sep. 15, 2011, Office Actions dated Apr. 5, 2010, Mar. 10, 2011, Apr. 11, 2011 and Jun. 15, 2011, and Applicant Responses filed Oct. 24, 2007, Jan. 5, 2010, Feb. 24, 2010, May 5, 2010, Apr. 6, 2011 and Sep. 15, 2011.
U.S. Appl. No. 11/410,555, filed Apr. 25, 2006: Partial electronic file history through Aug. 17, 2011, including Office Actions dated Sep. 10, 2010, Mar. 7, 2011 and May 23, 2011, and Applicant Responses filed Oct. 25, 2007, Jan. 5, 2010, Dec. 13, 2010, May 6, 2011 and Aug. 17, 2011.
U.S. Appl. No. 11/675,063, filed Feb. 14, 2007, now U.S. Pat. No. 828,728 Nov. 9, 2010: Partial electronic file history, including Office Actions dated Aug. 29, 2008, Dec. 3, 2008, Jun. 10, 2009, Feb. 19, 2010 and Jul. 26, 2010, and Applicant Responses filed Oct. 26, 2007, Oct. 7, 2008, Mar. 2, 2009, Nov. 13, 2009, Apr. 14, 2010 and Aug. 2, 2010.
U.S. Appl. No. 12/688,763, filed Jan. 15, 2010: Partial electronic file history through Jul. 27, 2011, including Office Actions dated Dec. 1, 2010, Apr. 26, 2011 and Jul. 27, 2011, and Applicant Responses filed Feb. 24, 2010, Feb. 17, 2011 and Jul. 25, 2011.

FIG. 5A - PRIOR ART

OXYGEN ENHANCING MEMBRANE SYSTEMS FOR IMPLANTABLE DEVICES

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/429,022, filed Feb. 9, 2017, which is a continuation of U.S. application Ser. No. 14/529,034, filed Oct. 30, 2014, now U.S. Pat. No. 9,597,027, which is a continuation of U.S. application Ser. No. 13/187,277, filed Jul. 20, 2011, now U.S. Pat. No. 8,909,314, which is a continuation of U.S. application Ser. No. 11/410,392 filed Apr. 25, 2006, now U.S. Pat. No. 8,255,033, which is a continuation of U.S. application Ser. No. 10/896,639 filed Jul. 21, 2004, now U.S. Pat. No. 7,379,765, which claims the benefit of priority under 35 U.S.C. § 119(e) to U.S. Provisional Application No. 60/490,009, filed Jul. 25, 2003. Each of the aforementioned applications is incorporated by reference herein in its entirety, and each is hereby expressly made a part of this specification.

FIELD OF THE INVENTION

The present invention relates generally to systems and methods for increasing oxygen availability in implantable devices.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically utilizes uncomfortable finger pricking methods. Due to the lack of comfort and convenience, a diabetic normally only measures his or her glucose level two to four times per day. Unfortunately, these time intervals are spread so far apart that the diabetic likely finds out too late, sometimes incurring dangerous side effects, of a hyperglycemic or hypoglycemic condition. In fact, it is not only unlikely that a diabetic will take a timely SMBG value, but additionally the diabetic will not know if their blood glucose value is going up (higher) or down (lower) based on conventional methods.

Consequently, a variety of transdermal and implantable electrochemical sensors are being developed for continuously detecting and/or quantifying blood glucose values. Many implantable glucose sensors suffer from complications within the body and provide only short-term or less-than-accurate sensing of blood glucose. Similarly, transdermal sensors have problems in accurately sensing and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have been observed.

SUMMARY OF THE PREFERRED EMBODIMENTS

Sensors that can provide accurate, real-time information under ischemic conditions are therefore desirable.

Accordingly, in a first embodiment, an electrochemical sensor for determining a presence or a concentration of an analyte in a fluid is provided, the sensor including a membrane system including an enzyme domain including an enzyme that reacts with the analyte in the fluid as it passes through the enzyme domain; and a working electrode including a conductive material, wherein the working electrode is configured to measure a product of a reaction of the enzyme with the analyte, wherein the membrane system includes a polymer material with a high oxygen solubility.

In an aspect of the first embodiment, the enzyme domain includes a polymer material with a high oxygen solubility.

In an aspect of the first embodiment, the polymer material is selected from the group consisting of silicone, fluorocarbon, and perfluorocarbon.

In an aspect of the first embodiment, the sensor further includes a resistance domain configured to restrict a flow of the analyte therethrough, wherein the resistance domain is located more distal to the working electrode than the enzyme domain, and wherein the resistance domain includes a polymer material with a high oxygen solubility.

In an aspect of the first embodiment, the resistance domain includes a polymer material selected from the group consisting of silicone, fluorocarbon, and perfluorocarbon.

In an aspect of the first embodiment, the sensor further includes a cell impermeable domain that is substantially impermeable to cells, wherein the cell impermeable domain is located more distal to the working electrode than the enzyme domain, and wherein the cell impermeable domain includes a polymer material with a high oxygen solubility.

In an aspect of the first embodiment, the cell impermeable domain includes a polymer material selected from the group consisting of silicone, fluorocarbon, and perfluorocarbon.

In an aspect of the first embodiment, the sensor further includes a cell disruptive domain that includes a substantially porous structure, wherein the cell disruptive domain is located more distal to the working electrode than the enzyme domain, and wherein the cell disruptive domain includes a polymer material with high oxygen solubility.

In an aspect of the first embodiment, the cell impermeable domain includes a polymer material selected from the group consisting of silicone, fluorocarbon, and perfluorocarbon.

In an aspect of the first embodiment, the sensor further includes an interference domain configured to limit or block interfering species, wherein the interference domain is located more proximal to the working electrode than the enzyme domain, and wherein the interference domain includes a polymer material with a high oxygen solubility.

In an aspect of the first embodiment, the interference domain includes a polymer material selected from the group consisting of silicone, fluorocarbon, and perfluorocarbon.

In an aspect of the first embodiment, the sensor further includes an electrolyte domain configured to provide hydrophilicity at the working electrode, wherein the electrolyte domain is located more proximal to the working electrode than the enzyme domain, and wherein the electrolyte domain includes a polymer material with a high oxygen solubility.

In an aspect of the first embodiment, the electrolyte domain includes a polymer material selected from the group consisting of silicone, fluorocarbon, and perfluorocarbon.

In a second embodiment, an analyte sensing device configured for implantation into a tissue of a host is provided, the device including an oxygen-utilizing source; a membrane system configured to provide at least one function selected from the group consisting of protection of the device from a biological environment; diffusion resistance of an analyte; a catalyst for enabling an enzymatic reaction; and limitation of interfering species; wherein the membrane system includes a polymer material with a high oxygen solubility, wherein the membrane system is adjacent to the oxygen-utilizing source.

In an aspect of the second embodiment, the oxygen-utilizing source includes an enzyme.

In an aspect of the second embodiment, the membrane system includes the polymer material with the high oxygen solubility, wherein the polymer material is substantially continuously situated between the enzyme and the tissue.

In an aspect of the second embodiment, the oxygen-utilizing source includes an electroactive surface.

In an aspect of the second embodiment, the membrane system includes the polymer material with the high oxygen solubility, wherein the polymer material is substantially continuously situated between the electroactive surface and the tissue.

In an aspect of the second embodiment, the oxygen-utilizing source includes cells.

In an aspect of the second embodiment, the membrane system includes the polymer material with the high oxygen solubility, wherein the polymer material is substantially continuously situated between the cells and the tissue.

In an aspect of the second embodiment, the polymer material is selected from the group consisting of silicone, fluorocarbon, and perfluorocarbon.

BRIEF DESCRIPTION OF THE DRAWINGS

FIG. 5A is a schematic diagram of oxygen concentration profiles through a prior art membrane.

DETAILED DESCRIPTION OF THE PREFERRED EMBODIMENT

Figure 1:
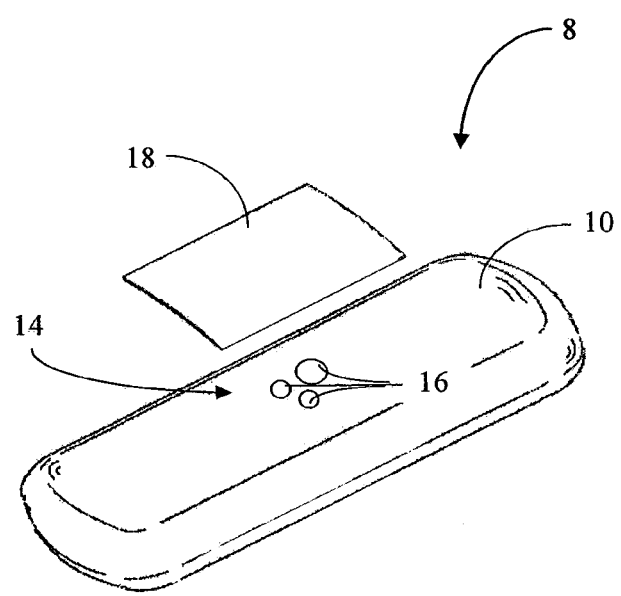
FIG. 1 is an exploded perspective view of an implantable glucose sensor in one exemplary embodiment.

The following description and examples illustrate some exemplary embodiments of the disclosed invention in detail.

Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxy-progesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "operable connection," "operably connected," and "operably linked" as used herein are broad terms and are used in their ordinary sense, including, without limitation, one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "host" as used herein is a broad term and is used in its ordinary sense, including, without limitation, mammals, particularly humans.

The terms "electrochemically reactive surface" and "electroactive surface" as used herein are broad terms and are used in their ordinary sense, including, without limitation, the surface of an electrode where an electrochemical reaction takes place. As one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, 02 is reduced at the electrode surface in order to balance the current being generated by the working electrode.

The term "sensing region" as used herein is a broad term and is used in its ordinary sense, including, without limitation, the region of a monitoring device responsible for the detection of a particular analyte. The sensing region generally comprises a non-conductive body, a working electrode, a reference electrode, and/or a counter electrode (optional) passing through and secured within the body forming electrochemically reactive surfaces on the body, an electronic connective means at another location on the body, and a multi-domain membrane affixed to the body and covering the electrochemically reactive surface.

The terms "raw data stream" and "data stream," as used herein, are broad terms and are used in their ordinary sense, including, without limitation, an analog or digital signal directly related to the measured glucose concentration from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term "electrical potential," as used herein, is a broad term and is used in its ordinary sense, including, without limitation, the electrical potential difference between two points in a circuit which is the cause of the flow of a current.

The term "ischemia," as used herein, is a broad term and is used in its ordinary sense, including, without limitation, local and temporary deficiency of blood supply due to obstruction of circulation to a part (for example, sensor). Ischemia can be caused by mechanical obstruction (for example, arterial narrowing or disruption) of the blood supply, for example.

The term "system noise," as used herein, is a broad term and is used in its ordinary sense, including, without limitation, unwanted electronic or diffusion-related noise which can include Gaussian, motion-related, flicker, kinetic, or other white noise, for example.

The terms "signal artifacts" and "transient non-glucose related signal artifacts," as used herein, are broad terms and are used in their ordinary sense, including, without limitation, signal noise that is caused by substantially non-glucose reaction rate-limiting phenomena, such as ischemia, pH changes, temperature changes, pressure, and stress, for example. Signal artifacts, as described herein, are typically transient and are characterized by higher amplitude than system noise.

The terms "low noise," as used herein, is a broad term and is used in its ordinary sense, including, without limitation, noise that substantially decreases signal amplitude.

The terms "high noise" and "high spikes," as used herein, are broad terms and are used in their ordinary sense, including, without limitation, noise that substantially increases signal amplitude.

The term "silicone composition" as used herein is a broad term and is used in its ordinary sense, including, without limitation, a composition of matter that comprises polymers having at least silicon and oxygen atoms in the backbone.

The phrase "distal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell disruptive domain is positioned farther from the sensor, then that domain is distal to the sensor.

The phrase "proximal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell impermeable domain is positioned nearer to the sensor, then that domain is proximal to the sensor.

The terms "interferants" and "interfering species," as used herein, are broad terms and are used in their ordinary sense, including, but not limited to, effects and/or species that interfere with the measurement of an analyte of interest in a sensor to produce a signal that does not accurately represent the analyte measurement. In an electrochemical sensor, interfering species can include compounds with an oxidation potential that overlaps with that of the analyte to be measured.

As employed herein, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade).

Overview

Membrane systems of the preferred embodiments are suitable for use with implantable devices in contact with a biological fluid. For example, the membrane systems can be utilized with implantable devices such as devices for monitoring and determining analyte levels in a biological fluid, for example, glucose levels for individuals having diabetes. In some embodiments, the analyte-measuring device is a continuous device. Alternatively, the device can analyze a plurality of intermittent biological samples. The analyte-measuring device can use any method of analyte-measurement, including enzymatic, chemical, physical, electrochemical, spectrophotometric, polarimetric, calorimetric, radiometric, or the like.

Although some of the description that follows is directed at glucose-measuring devices, including the described membrane systems and methods for their use, these membrane systems are not limited to use in devices that measure or monitor glucose. These membrane systems are suitable for use in a variety of devices, including, for example, those that detect and quantify other analytes present in biological fluids (including, but not limited to, cholesterol, amino acids, alcohol, galactose, and lactate), cell transplantation devices (see, for example, U.S. Pat. Nos. 6,015,572, 5,964,745, and 6,083,523), drug delivery devices (see, for example, U.S. Pat. Nos. 5,458,631, 5,820,589, and 5,972,369), and the like. Preferably, implantable devices that include the membrane systems of the preferred embodiments are implanted in soft tissue, for example, abdominal, subcutaneous, and peritoneal tissues, the brain, the intramedullary space, and other suitable organs or body tissues.

In addition to the glucose-measuring device described below, the membrane systems of the preferred embodiments can be employed with a variety of known glucose measuring-devices. In some embodiments, the electrode system can be used with any of a variety of known in vivo analyte sensors or monitors, such as U.S. Pat. No. 6,001,067 to Shults et al.; U.S. Pat. No. 6,702,857 to Brauker et al.; U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. 5,985,129 to Gough et al.; WO Patent Application Publication No. 04/021877 to Caduff; U.S. Pat. No. 5,494,562 to Maley et al.; U.S. Pat. No. 6,120,676 to Heller et al.; and U.S. Pat. No. 6,542,765 to Guy et al., each of which are incorporated in there entirety herein by reference. In general, it is understood that the disclosed embodiments are applicable to a variety of continuous glucose measuring device configurations.

FIG. 1 is an exploded perspective view of one exemplary embodiment comprising an implantable glucose sensor 10 that utilizes amperometric electrochemical sensor technology to measure glucose. In this exemplary embodiment, a body 12 with a sensing region 14 includes an electrode system 16 and sensor electronics, which are described in more detail with reference to FIG. 2.

In this embodiment, the electrode system 16 is operably connected to the sensor electronics (FIG. 2) and includes electroactive surfaces, which are covered by a membrane system 18. The membrane system 18 is disposed over the electroactive surfaces of the electrode system 16 and provides one or more of the following functions: 1) protection of the exposed electrode surface from the biological environment (cell impermeable domain); 2) diffusion resistance (limitation) of the analyte (resistance domain); 3) a catalyst for enabling an enzymatic reaction (enzyme domain); 4) limitation or blocking of interfering species (interference domain); and/or 5) hydrophilicity at the electrochemically reactive surfaces of the sensor interface (electrolyte domain), for example, as described in co-pending U.S. patent application Ser. No. 10/838,912, filed May 3, 2004 and entitled "IMPLANTABLE ANALYTE SENSOR," the contents of which are hereby incorporated herein by reference in their entirety. The membrane system can be attached to the sensor body 12 by mechanical or chemical methods such as are described in co-pending U.S. Patent Application MEMBRANE ATTACHMENT and U.S. patent application Ser. No. 10/838,912 filed May 3, 2004 and entitled, "IMPLANTABLE ANALYTE SENSOR", the contents of which are hereby incorporated herein by reference in their entirety.

Figure 3:
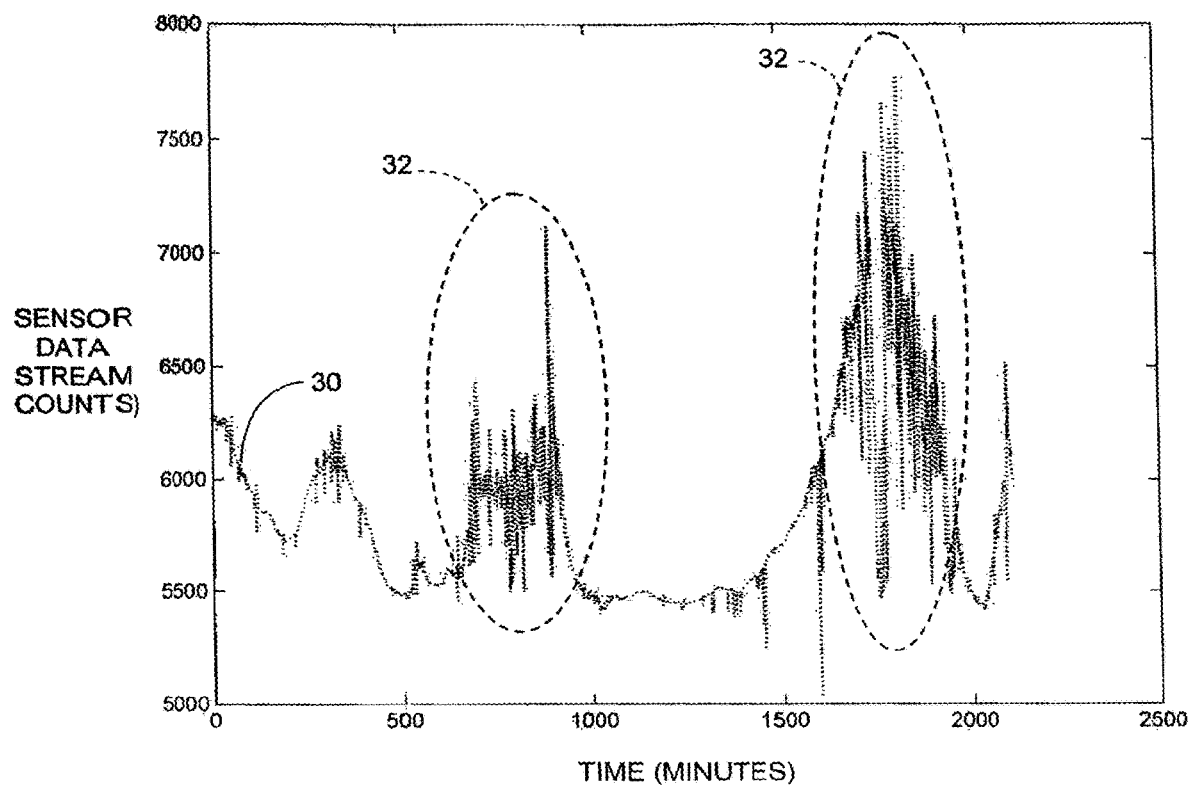
FIG. 3 is a graph that shows a raw data stream obtained from a glucose sensor over a 36-hour time span in one example.
Figure 4:
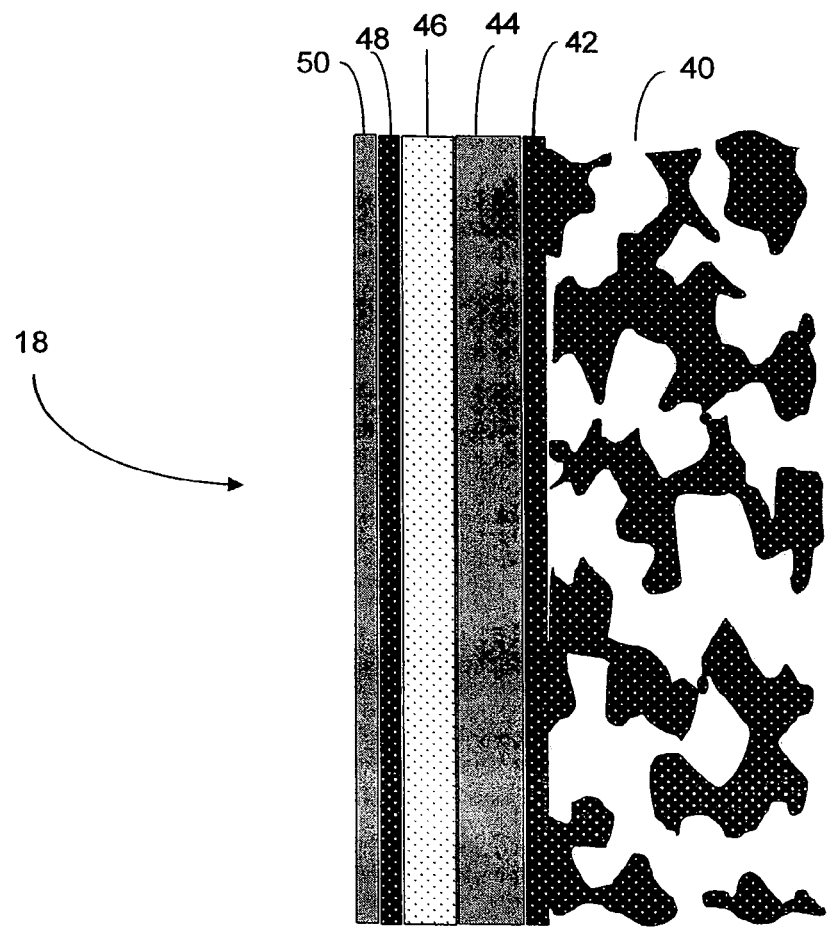
FIG. 4 is a schematic illustration of a membrane system of the device of FIG. 1.
Figure 5B:
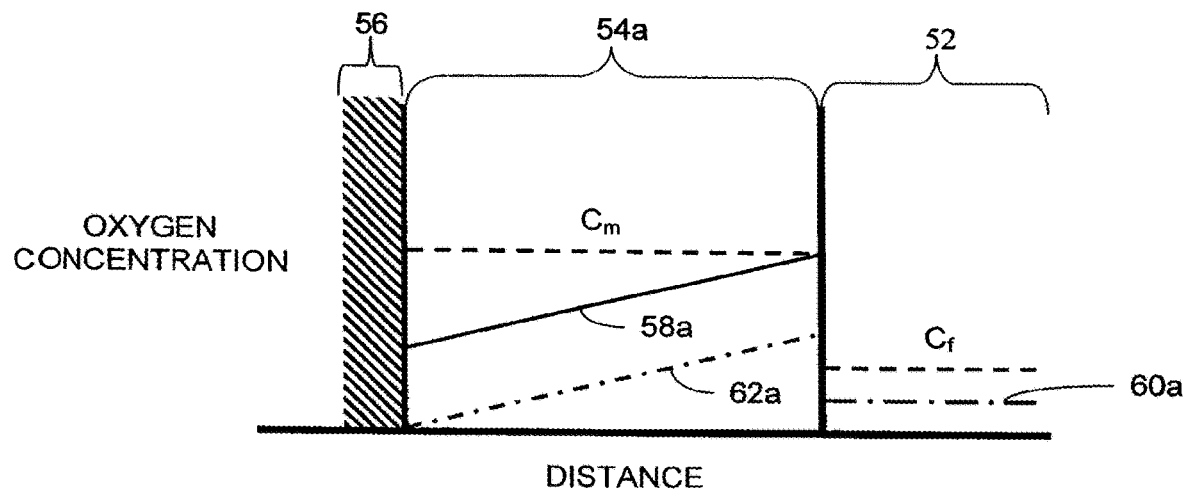
FIG. 5B is a schematic diagram of oxygen concentration profiles through the membrane system of the preferred embodiments.
Figure 5B:
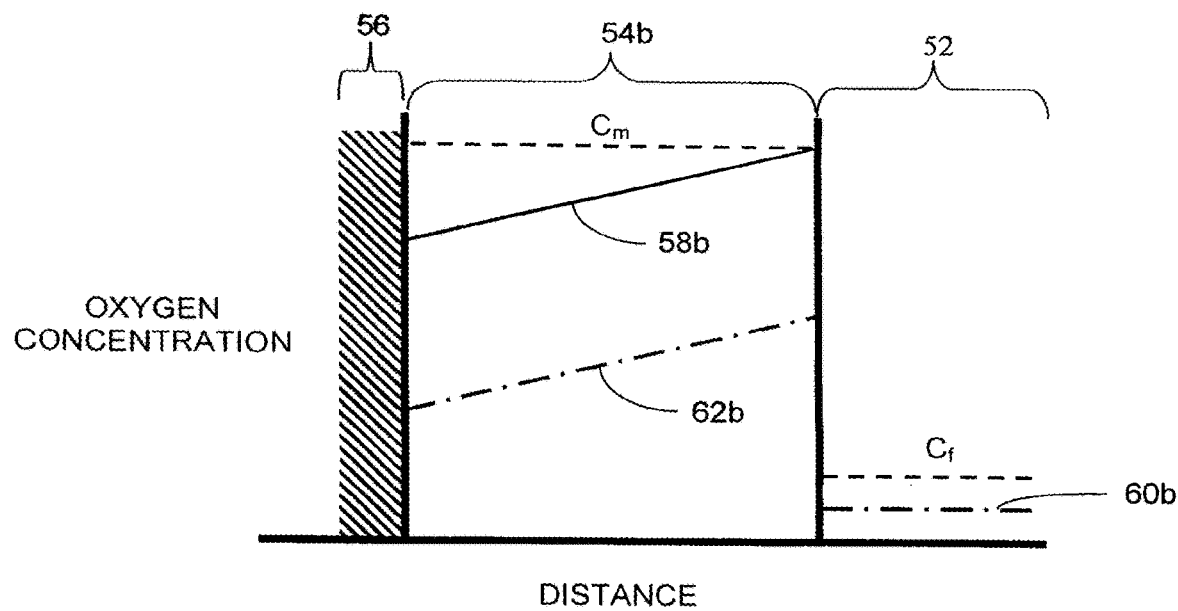

The membrane system 18 of the preferred embodiments, which are described in more detail below with reference to FIGS. 4 and 5, is formed at least partially from materials with high oxygen solubility. These materials act as a high oxygen soluble domain, dynamically retaining a high availability of oxygen that can be used to compensate for the local oxygen deficit during times of transient ischemia, which is described in more detail below and with reference to FIG. 3. As a result, the membrane systems of the preferred embodiments enable glucose sensors and other implantable devices such as cell transplantation devices to function in the subcutaneous space even during local transient ischemia.

In some embodiments, the electrode system 16, which is located on or within the sensing region 14, is comprised of at least a working and a reference electrode with an insulating material disposed therebetween. In some alternative embodiments, additional electrodes can be included within the electrode system, for example, a three-electrode system (working, reference, and counter electrodes) and/or including an additional working electrode (which can be used to generate oxygen, measure an additional analyte, or can be configured as a baseline subtracting electrode, for example).

In the exemplary embodiment of FIG. 1, the electrode system includes three electrodes (working, counter, and reference electrodes), wherein the counter electrode is provided to balance the current generated by the species being measured at the working electrode. In the case of a glucose oxidase based glucose sensor, the species being measured at the working electrode is $H_2O_2$. Glucose oxidase, GOX, catalyzes the conversion of oxygen and glucose to hydrogen peroxide and gluconate according to the following reaction:

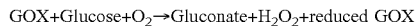

GOX+Glucose+$O_2$→Gluconate+$H_2O_2$+reduced GOX

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$). In such embodiments, because the counter electrode utilizes oxygen as an electron acceptor, the most likely reducible species for this system are oxygen or enzyme generated peroxide. There are two main pathways by which oxygen can be consumed at the counter electrode. These pathways include a four-electron pathway to produce hydroxide and a two-electron pathway to produce hydrogen peroxide. In addition to the counter electrode, oxygen is further consumed by the reduced glucose oxidase within the enzyme domain. Therefore, due to the oxygen consumption by both the enzyme and the counter electrode, there is a net consumption of oxygen within the electrode system. Theoretically, in the domain of the working electrode there is significantly less net loss of oxygen than in the region of the counter electrode. In addition, there is a close correlation between the ability of the counter electrode to maintain current balance and sensor function.

In general, in electrochemical sensors wherein an enzymatic reaction depends on oxygen as a co-reactant, depressed function or inaccuracy can be experienced in low oxygen environments, for example in vivo. Subcutaneously implanted devices are especially susceptible to transient ischemia that can compromise device function; for example, because of the enzymatic reaction required for an implantable amperometric glucose sensor, oxygen must be in excess over glucose in order for the sensor to effectively function as a glucose sensor. If glucose becomes in excess, the sensor turns into an oxygen sensitive device. In vivo, glucose concentration can vary from about one hundred times or more that of the oxygen concentration. Consequently, oxygen becomes a limiting reactant in the electrochemical reaction and when insufficient oxygen is provided to the sensor, the sensor is unable to accurately measure glucose concentration. Those skilled in the art interpret oxygen limitations resulting in depressed function or inaccuracy as a problem of availability of oxygen to the enzyme and/or counter electrode. Oxygen limitations can also be seen during periods of transient ischemia that occur, for example, under certain postures or when the region around the implanted sensor is compressed so that blood is forced out of the capillaries. Such ischemic periods observed in implanted sensors can last for many minutes or even an hour or longer.

Figure 2:
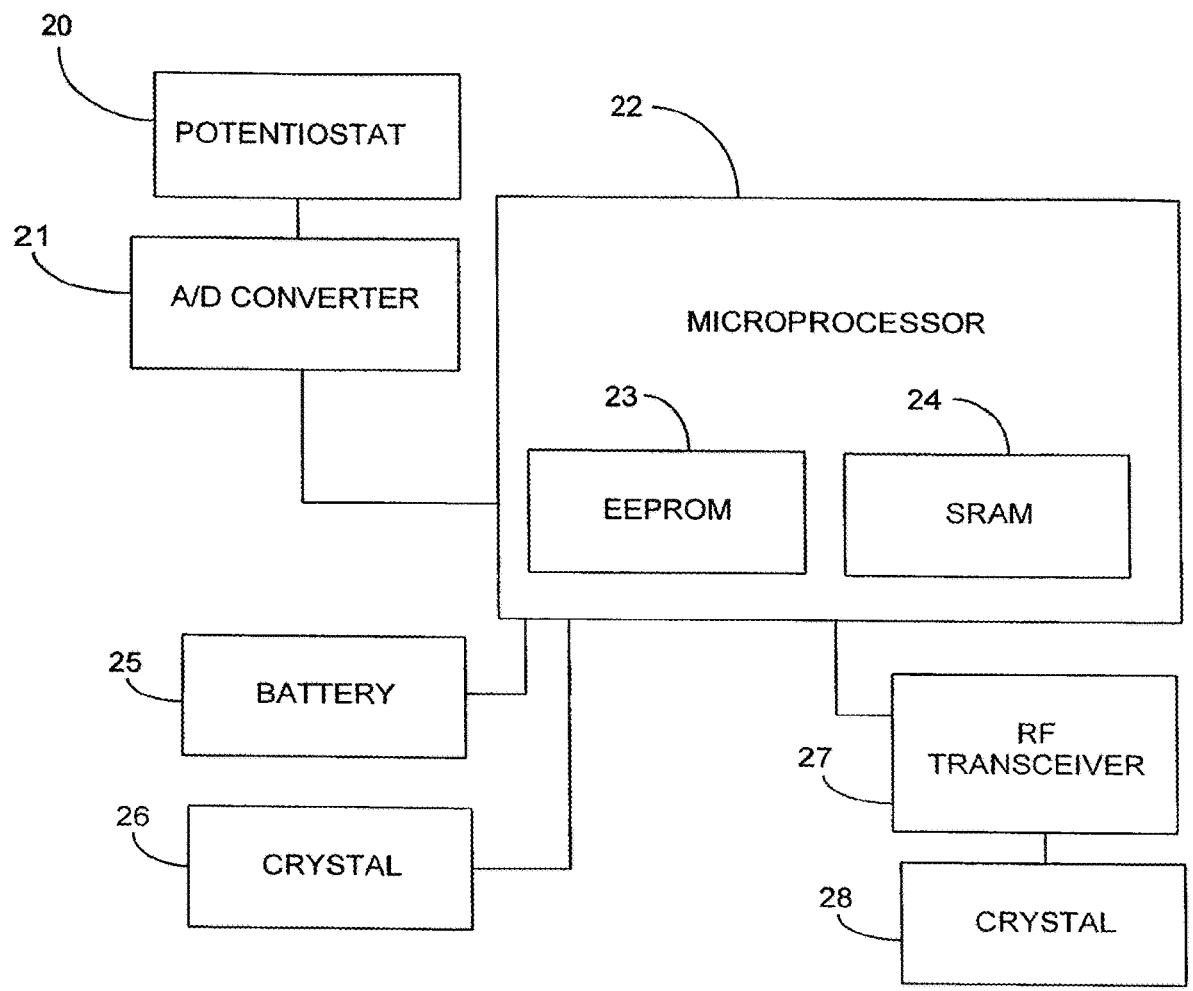
FIG. 2 is a block diagram that illustrates the sensor electronics in one embodiment; however a variety of sensor electronics configurations can be implemented with the preferred embodiments.

FIG. 2 is a block diagram that illustrates sensor electronics in one exemplary embodiment; one skilled in the art appreciates, however, a variety of sensor electronics configurations can be implemented with the preferred embodiments. In this embodiment, a potentiostat 20 is shown, which is operatively connected to electrode system 16 (FIG. 1) to obtain a current value, and includes a resistor (not shown) that translates the current into voltage. The A/D converter 21 digitizes the analog signal into "counts" for processing. Accordingly, the resulting raw data signal in counts is directly related to the current measured by the potentiostat.

A microprocessor 22 is the central control unit that houses EEPROM 23 and SRAM 24, and controls the processing of the sensor electronics. The alternative embodiments can utilize a computer system other than a microprocessor to process data as described herein. In some alternative embodiments, an application-specific integrated circuit (ASIC) can be used for some or all the sensor's central processing. EEPROM 23 provides semi-permanent storage of data, storing data such as sensor ID and programming to process data signals (for example, programming for data smoothing such as described elsewhere herein). SRAM 24 is used for the system's cache memory, for example for temporarily storing recent sensor data.

The battery 25 is operatively connected to the microprocessor 22 and provides the power for the sensor. In one embodiment, the battery is a Lithium Manganese Dioxide battery, however any appropriately sized and powered battery can be used. In some embodiments, a plurality of batteries can be used to power the system. Quartz Crystal 26 is operatively connected to the microprocessor 22 and maintains system time for the computer system.

The RF Transceiver 27 is operably connected to the microprocessor 22 and transmits the sensor data from the sensor to a receiver. Although a RF transceiver is shown here, some other embodiments can include a wired rather than wireless connection to the receiver. In yet other embodiments, the sensor can be transcutaneously connected via an inductive coupling, for example. The quartz crystal 28 provides the system time for synchronizing the data transmissions from the RF transceiver. The transceiver 27 can be substituted with a transmitter in one embodiment.

Although FIGS. 1 to 2 and associated text illustrate and describe one exemplary embodiment of an implantable glucose sensor, the electrode system, electronics and its method of manufacture of the preferred embodiments described below can be implemented on any known electrochemical sensor, including those described in co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; "OPTIMIZED SENSOR GEOMETRY FOR AN IMPLANTABLE GLUCOSE SENSOR"; U.S. application Ser. No. 10/633,367 filed Aug. 1, 2003 entitled, "SYSTEM AND METHODS FOR PROCESSING ANALYTE SEN- SOR DATA", the contents of each of which are hereby incorporated by reference in their entireties.

FIG. 3 is a graph that shows a raw data stream obtained from a glucose sensor with a conventional membrane system. The x-axis represents time in minutes. The y-axis represents sensor data in counts. In this example, sensor output in counts is transmitted every 30 seconds. The raw data stream 30 includes substantially smooth sensor output in some portions, however other portions exhibit transient non-glucose related signal artifacts 32.

The raw data stream 30 includes substantially smooth sensor output in some portions, however other portions exhibit erroneous or transient non-glucose related signal artifacts 32. Particularly, referring to the signal artifacts 32, it is believed that effects of local ischemia on prior art electrochemical sensors creates erroneous (non-glucose) signal values due to oxygen deficiencies either at the enzyme within the membrane system and/or at the counter electrode on the electrode surface.

In one situation, when oxygen is deficient relative to the amount of glucose, the enzymatic reaction is limited by oxygen rather than glucose. Thus, the output signal is indicative of the oxygen concentration rather than the glucose concentration, producing erroneous signals. Additionally, when an enzymatic reaction is rate-limited by oxygen, glucose is expected to build up in the membrane because it is not completely catabolized during the oxygen deficit. When oxygen is again in excess, there is also excess glucose due to the transient oxygen deficit. The enzyme rate then speeds up for a short period until the excess glucose is catabolized, resulting in spikes of non-glucose related increased sensor output. Accordingly, because excess oxygen (relative to glucose) is necessary for proper sensor function, transient ischemia can result in a loss of signal gain in the sensor data.

In another situation, oxygen deficiency can be seen at the counter electrode when insufficient oxygen is available for reduction, which thus affects the counter electrode in that it is unable to balance the current coming from the working electrode. When insufficient oxygen is available for the counter electrode, the counter electrode can be driven in its electrochemical search for electrons all the way to its most negative value, which can be ground, or 0.0 V, which causes the reference to shift, reducing the bias voltage such as is described in more detail below. In other words, a common result of ischemia is seen as a drop off in sensor current as a function of glucose concentration (for example, lower sensitivity). This occurs because the working electrode no longer oxidizes all of the $H_2O_2$ arriving at its surface because of the reduced bias. In some extreme circumstances, an increase in glucose can produce no increase in current or even a decrease in current.

In some situations, transient ischemia can occur at high glucose levels, wherein oxygen can become limiting to the enzymatic reaction, resulting in a non-glucose dependent downward trend in the data. In some situations, certain movements or postures taken by the patient can cause transient signal artifacts as blood is squeezed out of the capillaries, resulting in local ischemia, and causing non-glucose dependent signal artifacts. In some situations, oxygen can also become transiently limited due to contracture of tissues around the sensor interface. This is similar to the blanching of skin that can be observed when one puts pressure on it. Under such pressure, transient ischemia can occur in both the epidermis and subcutaneous tissue. Transient ischemia is common and well tolerated by subcutaneous tissue. However, such ischemic periods can cause an oxygen deficit in implanted devices that can last for many minutes or even an hour or longer.

Although some examples of the effects of transient ischemia on a prior art glucose sensor are described above, similar effects can be seen with analyte sensors that use alternative catalysts to detect other analytes, for example, amino acids (amino acid oxidase), alcohol (alcohol oxidase), galactose (galactose oxidase), lactate (lactate oxidase), and cholesterol (cholesterol oxidase), or the like.

Membrane Systems of the Preferred Embodiments

In order to overcome the effects of transient ischemia, the membrane systems 18 of the preferred embodiments include materials with high oxygen solubility. These materials increase the local amount of oxygen to aid in compensating for local oxygen deficits during ischemic conditions. As a result, the membrane systems of the preferred embodiments enable analyte sensors and other devices such as cell transplantation devices to function in the subcutaneous space even during local transient ischemia.

The phrases "high oxygen solubility" and "high oxygen soluble" as used herein are broad phrases and are used in their ordinary sense, including, without limitation, a domain or material property that includes higher oxygen solubility than aqueous media so that it concentrates oxygen from the biological fluid surrounding the membrane system. In some preferred embodiments, a high oxygen solubility polymer has at least about 3× higher oxygen solubility than aqueous media, more preferably at least about 4×, 5×, or 6× higher oxygen solubility than aqueous media, and most preferably at least about 7×, 8×, 9×, 10× or more higher oxygen solubility than aqueous media. In one embodiment, high oxygen solubility is defined as having higher oxygen solubility than at least one of a hydrocarbonaceous polymer and an oxyhydrocarbon polymer (a hydrocarbonaceous polymer is a polymeric material consisting of carbon and hydrogen atoms and an oxyhydrocarbonaceous polymer is a polymeric material consisting of carbon, hydrogen, and oxygen atoms). Oxygen solubility can be measured using any known technique, for example by removing the oxygen from the polymer (namely, solution) via at least three Freeze-Pump-Thaw cycles and then measuring the resultant oxygen (for example, using a manometer).

Oxygen permeability (Dk) is calculated as diffusion multiplied by solubility. Oxygen Permeability is conveniently reported in units of Barrers (1 Barrer=$10^{-10}$ cm$^3$ O$_2$ (STP) cm/cm$^2$ s cmHg). Insulating materials of preferred embodiments that have a high oxygen permeability typically have an oxygen permeability of from about 1 Barrer or less to about 1000 Barrers or more, preferably from about 1, 2, 3, 4, 5, 6, 7, 8, 9, 10, 15, 20, 25, 30, 35, 40, 45, 50, 55, 60, 65, 70, 75, 80, 85, 90, 95, or 100 Barrers to about 125, 150, 175, 200, 225, 250, 275, 300, 325, 350, 375, 400, 425, 450, 475, 500, 550, 600, 650, 700, 750, 800, 850, 900, or 950 Barrers.

In one exemplary embodiment, the properties of silicone (and/or silicone compositions) inherently enable materials formed from silicone to act as a high oxygen solubility domain. Utilization of a high oxygen soluble material in an electrochemical sensor is advantageous because it is believed to dynamically retain high oxygen availability to oxygen-utilizing sources (for example, an enzyme and/or a counter electrode of an electrochemical cell).

As described below with reference to FIG. 4, the membrane system 18 can include two or more domains that cover an implantable device, for example, an implantable glucose sensor. In the example of an implantable enzyme-based electrochemical glucose sensor, the membrane prevents direct contact of the biological fluid sample with the electrodes, while controlling the permeability of selected substances (for example, oxygen and glucose) present in the biological fluid through the membrane for reaction in an enzyme rich domain with subsequent electrochemical reaction of formed products at the electrodes.

The membrane systems of preferred embodiments are constructed of two or more domains. The multi-domain membrane can be formed from one or more distinct layers and can comprise the same or different materials. The term "domain" is a broad term and is used in its ordinary sense, including, without limitation, a single homogeneous layer or region that incorporates the combined functions one or more domains, or a plurality of layers or regions that each provide one or more of the functions of each of the various domains.

FIG. 4 is an illustration of a membrane system in one preferred embodiment. The membrane system 18 can be used with a glucose sensor such, as is described above with reference to FIG. 1. In this embodiment, the membrane system 18 includes a cell disruptive domain 40 most distal of all domains from the electrochemically reactive surfaces, a cell impermeable domain 42 less distal from the electrochemically reactive surfaces than the cell disruptive domain, a resistance domain 44 less distal from the electrochemically reactive surfaces than the cell impermeable domain, an enzyme domain 46 less distal from the electrochemically reactive surfaces than the resistance domain, an interference domain 48 less distal from the electrochemically reactive surfaces than the enzyme domain, and an electrolyte domain 50 adjacent to the electrochemically reactive surfaces. However, it is understood that the membrane system can be modified for use in other devices, by including only two or more of the domains, or additional domains not recited above.

In some embodiments, the membrane system is formed as a homogeneous membrane, namely, a membrane having substantially uniform characteristics from one side of the membrane to the other. However, a membrane can have heterogeneous structural domains, for example, domains resulting from the use of block copolymers (for example, polymers in which different blocks of identical monomer units alternate with each other), but can be defined as homogeneous overall in that each of the above-described domains functions by the preferential diffusion of some substance through the homogeneous membrane.

In the preferred embodiments, one or more of the above-described domains are formed from high oxygen solubility material. Utilization of high oxygen solubility material is advantageous because it is believed to dynamically retain a higher amount of oxygen, which maintains higher oxygen availability to selected locations (for example, the enzyme and/or counter electrode). In some embodiments, the high oxygen soluble material includes silicones, fluorocarbons, perfluorocarbons, or the like. In one embodiment, one or more domains is/are formed from a silicone composition that allows the transport of glucose other such water-soluble molecules (for example, drugs), such as are described in more detail with reference to co-pending U.S. application Ser. No. 10/685,636 filed Oct. 28, 2003 and entitled, "SILICONE COMPOSITION FOR MEMBRANE SYSTEM," the contents of which are hereby incorporated by reference in their entireties.

Cell Disruptive Domain

The cell disruptive domain 40 is positioned most distal to the implantable device and is designed to support tissue ingrowth, to disrupt contractile forces typically found in a foreign body capsule, to encourage vascularity within the membrane, and/or to disrupt the formation of a barrier cell layer. In one embodiment, the cell disruptive domain 40 has an open-celled configuration with interconnected cavities and solid portions, wherein the distribution of the solid portion and cavities of the cell disruptive domain includes a substantially co-continuous solid domain and includes more than one cavity in three dimensions substantially throughout the entirety of the first domain. Cells can enter into the cavities; however they cannot travel through or wholly exist within the solid portions. The cavities allow most substances to pass through, including, for example, cells, and molecules. U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, and entitled, "POROUS MEMBRANES FOR USE WITH IMPLANTABLE DEVICES" describe membranes having a cell disruptive domain.

The cell disruptive domain 40 is preferably formed from high oxygen soluble materials such as polymers formed from silicone, fluorocarbons, perfluorocarbons, or the like. In one embodiment, the cell disruptive domain is formed from a silicone composition with a non-silicon containing hydrophile such as such as polyethylene glycol, propylene glycol, pyrrolidone, esters, amides, carbonates, or polypropylene glycol covalently incorporated or grafted therein. In some alternative embodiments, the cell disruptive domain is formed from polyethylene-co-tetrafluoroethylene, polyolefin, polyester, polycarbonate, biostable polytetrafluoroethylene, homopolymers, copolymers, terpolymers of polytetrafluoroethylene, polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones or block copolymers thereof including, for example, di-block, tri-block, alternating, random and graft copolymers.

In preferred embodiments, the thickness of the cell disruptive domain is from about 10 or less, 20, 30, 40, 50, 60, 70, 80, or 90 microns to about 1500, 2000, 2500, or 3000 or more microns. In more preferred embodiments, the thickness of the cell disruptive domain is from about 100, 150, 200 or 250 microns to about 1000, 1100, 1200, 1300, or 1400 microns. In even more preferred embodiments, the thickness of the cell disruptive domain is from about 300, 350, 400, 450, 500, or 550 microns to about 500, 550, 600, 650, 700, 750, 800, 850, or 900 microns.

The cell disruptive domain is optional and can be omitted when using an implantable device that does not prefer tissue ingrowth, for example, a short-lived device (for example, less than one day to about a week) or one that delivers tissue response modifiers.

Cell Impermeable Domain

The cell impermeable domain 42 is positioned less distal to the implantable device than the cell disruptive domain, and can be resistant to cellular attachment, impermeable to cells, and/or is composed of a biostable material. When the cell impermeable domain is resistant to cellular attachment (for example, attachment by inflammatory cells, such as macrophages, which are therefore kept a sufficient distance from other domains, for example, the enzyme domain), hypochlorite and other oxidizing species are short-lived chemical species in vivo, and biodegradation does not occur. Additionally, the materials preferred for forming this domain are resistant to the effects of these oxidative species and have thus been termed biodurable. See, for example, U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, and entitled, "POROUS MEMBRANES FOR USE WITH IMPLANTABLE DEVICES."

The cell impermeable domain 42 is preferably formed from high oxygen soluble materials such as polymers formed from silicone, fluorocarbons, perfluorocarbons, or the like. In one embodiment, the cell impermeable domain is formed from a silicone composition with a hydrophile such as such as polyethylene glycol, propylene glycol, pyrrolidone, esters, amides, carbonates, or polypropylene glycol covalently incorporated or grafted therein. In some alternative embodiments, the cell impermeable domain is formed from copolymers or blends of copolymers with hydrophilic polymers such as polyvinylpyrrolidone (PVP), polyhydroxyethyl methacrylate, polyvinylalcohol, polyacrylic acid, polyethers such as polyethylene glycol, and block copolymers thereof, including, for example, di-block, tri-block, alternating, random and graft copolymers (block copolymers are discussed in U.S. Pat. Nos. 4,803,243 and 4,686,044).

In preferred embodiments, the thickness of the cell impermeable domain is from about 10 or 15 microns or less to about 125, 150, 175, or 200 microns or more. In more preferred embodiments, the thickness of the cell impermeable domain is from about 20, 25, 30, or 35 microns to about 65, 70, 75, 80, 85, 90, 95, or 100 microns. In even more preferred embodiments, the cell impermeable domain is from about 40 or 45 microns to about 50, 55, or 60 microns thick.

The cell disruptive domain 40 and cell impermeable domain 42 of the membrane system can be formed together as one unitary structure. Alternatively, the cell disruptive and cell impermeable domains 40, 42 of the membrane system can be formed as two layers mechanically or chemically bonded together.

Resistance Domain

The resistance domain 44 is situated more proximal to the implantable device relative to the cell disruptive domain. The resistance domain controls the flux of oxygen and other analytes (for example, glucose) to the underlying enzyme domain. As described in more detail elsewhere herein, there exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based sensor employing oxygen as cofactor is supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels can be obtained only up to about 40 mg/dL. However, in a clinical setting, a linear response to glucose levels is desirable up to at least about 500 mg/dL.

The resistance domain 44 includes a semipermeable membrane that controls the flux of oxygen and glucose to the underlying enzyme domain 46, preferably rendering oxygen in non-rate-limiting excess. As a result, the upper limit of linearity of glucose measurement is extended to a much higher value than that which is achieved without the resistance domain. In one embodiment, the resistance domain 44 exhibits an oxygen-to-glucose permeability ratio of approximately 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)). In some embodiments, a lower ratio of oxygen-to-glucose can be sufficient to provide excess oxygen by using a high oxygen soluble domain (for example, a silicone material) to enhance the supply/transport of oxygen to the enzyme membrane and/or electroactive surfaces. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess.

The resistance domain 44 is preferably formed from high oxygen soluble materials such as polymers formed from silicone, fluorocarbons, perfluorocarbons, or the like. In one embodiment, the resistance domain is formed from a silicone composition with a hydrophile such as such as polyethylene glycol, propylene glycol, pyrrolidone, esters, amides, carbonates, or polypropylene glycol covalently incorporated or grafted therein. In some alternative embodiments, the resistance domain is from polyurethane, for example, a polyurethane urea/polyurethane-block-polyethylene glycol blend.

In some embodiments, the resistance domain 44 can be formed as a unitary structure with the cell impermeable domain 42; that is, the inherent properties of the resistance domain 44 can provide the functionality described with reference to the cell impermeable domain 42 such that the cell impermeable domain 42 is incorporated as a part of resistance domain 44. In these embodiments, the combined resistance domain/cell impermeable domain can be bonded to or formed as a skin on the cell disruptive domain 40 during a molding process such as described above. In another embodiment, the resistance domain 44 is formed as a distinct layer and chemically or mechanically bonded to the cell disruptive domain 40 (if applicable) or the cell impermeable domain 42 (when the resistance domain is distinct from the cell impermeable domain).

In preferred embodiments, the thickness of the resistance domain is from about 10 microns or less to about 200 microns or more. In more preferred embodiments, the thickness of the resistance domain is from about 15, 20, 25, 30, or 35 microns to about 65, 70, 75, 80, 85, 90, 95, or 100 microns. In more preferred embodiments, the thickness of the resistance domain is from about 40 or 45 microns to about 50, 55, or 60 microns.

Enzyme Domain

An immobilized enzyme domain 46 is situated less distal from the electrochemically reactive surfaces than the resistance domain 44. In one embodiment, the immobilized enzyme domain 46 comprises glucose oxidase. In other embodiments, the immobilized enzyme domain 46 can be impregnated with other oxidases, for example, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration.

The enzyme domain 44 is preferably formed from high oxygen soluble materials such as polymers formed from silicone, fluorocarbons, perfluorocarbons, or the like. In one embodiment, the enzyme domain is formed from a silicone composition with a hydrophile such as such as polyethylene glycol, propylene glycol, pyrrolidone, esters, amides, carbonates, or polypropylene glycol covalently incorporated or grafted therein.

In one preferred embodiment, high oxygen solubility within the enzyme domain can be achieved by using a polymer matrix to host the enzyme within the enzyme domain, which has a high solubility of oxygen. In one exemplary embodiment of fluorocarbon-based polymers, the solubility of oxygen within a perfluorocarbon-based polymer is 50-volume %. As a reference, the solubility of oxygen in water is approximately 2-volume %.

Utilization of a high oxygen solubility material for the enzyme domain is advantageous because the oxygen dissolves more readily within the domain and thereby acts as a high oxygen soluble domain optimizing oxygen availability to oxygen-utilizing sources (for example, the enzyme and/or counter electrode). When the resistance domain 44 and enzyme domain 46 both comprise a high oxygen soluble material, the chemical bond between the enzyme domain 46 and resistance domain 44 can be optimized, and the manufacturing made easy.

In preferred embodiments, the thickness of the enzyme domain is from about 1 micron or less to about 40, 50, 60, 70, 80, 90, or 100 microns or more. In more preferred embodiments, the thickness of the enzyme domain is between about 1, 2, 3, 4, or 5 microns and 13, 14, 15, 20, 25, or 30 microns. In even more preferred embodiments, the thickness of the enzyme domain is from about 6, 7, or 8 microns to about 9, 10, 11, or 12 microns.

Interference Domain

The interference domain 48 is situated less distal to the implantable device than the immobilized enzyme domain. Interferants are molecules or other species that are electro-reduced or electro-oxidized at the electrochemically reactive surfaces, either directly or via an electron transfer agent, to produce a false signal (for example, urate, ascorbate, or acetaminophen). In one embodiment, the interference domain 48 prevents the penetration of one or more interferants into the electrolyte phase around the electrochemically reactive surfaces. Preferably, this type of interference domain is much less permeable to one or more of the interferants than to the analyte.

In one embodiment, the interference domain 48 can include ionic components incorporated into a polymeric matrix to reduce the permeability of the interference domain to ionic interferants having the same charge as the ionic components. In another embodiment, the interference domain 48 includes a catalyst (for example, peroxidase) for catalyzing a reaction that removes interferants. U.S. Pat. Nos. 6,413,396 and 6,565,509 disclose methods and materials for eliminating interfering species; however in the preferred embodiments any suitable method or material can be employed.

In another embodiment, the interference domain 48 includes a thin membrane that is designed to limit diffusion of species, for example, those greater than 34 kD in molecular weight, for example. The interference domain permits analytes and other substances (for example, hydrogen peroxide) that are to be measured by the electrodes to pass through, while preventing passage of other substances, such as potentially interfering substances. In one embodiment, the interference domain 48 is constructed of polyurethane. In an alternative embodiment, the interference domain 48 comprises a high oxygen soluble polymer, such as described above.

In preferred embodiments, the thickness of the interference domain is from about 0.1 microns or less to about 10 microns or more. In more preferred embodiments, the thickness of the interference domain is between about 0.2, 0.3, 0.4, or 0.5 microns and about 5, 6, 7, 8, or 9 microns. In more preferred embodiments, the thickness of the interference domain is from about 0.6, 0.7, 0.8, 0.9, or 1 micron to about 2, 3, or 4 microns.

Electrolyte Domain

An electrolyte domain 50 is situated more proximal to the electrochemically reactive surfaces than the interference domain 48. To ensure the electrochemical reaction, the electrolyte domain 30 includes a semipermeable coating that maintains hydrophilicity at the electrochemically reactive surfaces of the sensor interface. The electrolyte domain 50 enhances the stability of the interference domain 48 by protecting and supporting the material that makes up the interference domain. The electrolyte domain also 50 assists in stabilizing the operation of the device by overcoming electrode start-up problems and drifting problems caused by inadequate electrolyte. The buffered electrolyte solution contained in the electrolyte domain also protects against pH-mediated damage that can result from the formation of a large pH gradient between the substantially hydrophobic interference domain and the electrodes due to the electrochemical activity of the electrodes. In some embodiments, the electrolyte domain may not be used, for example, when an interference domain is not provided.

In one embodiment, the electrolyte domain 50 includes a flexible, water-swellable, substantially solid gel-like film having a "dry film" thickness of from about 2.5 microns to about 12.5 microns, more preferably from about 3, 3.5, 4, 4.5, 5, or 5.5 to about 6, 6.5, 7, 7.5, 8, 8.5, 9, 9.5, 10, 10.5, 11, 11.5, or 12 microns. "Dry film" thickness refers to the thickness of a cured film cast from a coating formulation onto the surface of the membrane by standard coating techniques.

In some embodiments, the electrolyte domain 50 is formed of a curable mixture of a urethane polymer and a hydrophilic polymer. Particularly preferred coatings are formed of a polyurethane polymer having anionic carboxylate functional groups and non-ionic hydrophilic polyether segments, which is crosslinked in the presence of polyvinylpyrrolidone and cured at a moderate temperature of about 50° C. In some preferred embodiments, the electrolyte domain 50 is formed from high oxygen soluble materials such as polymers formed from silicone, fluorocarbons, perfluorocarbons, or the like.

In one preferred embodiment, the electrolyte domain 50 is formed from a high oxygen soluble material, such as described above. In preferred embodiments, the thickness of the electrolyte domain is from about 1 micron or less to about 40, 50, 60, 70, 80, 90, or 100 microns or more. In more preferred embodiments, the thickness of the electrolyte domain is from about 2, 3, 4, or 5 microns to about 15, 20, 25, or 30 microns. In even more preferred embodiments, the thickness of the electrolyte domain is from about 6, 7, or 8 microns to about 9, 10, 11, or 12 microns.

Underlying the electrolyte domain is an electrolyte phase is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrolyte domain. The devices of the preferred embodiments contemplate the use of any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

In various embodiments, any of these domains can be omitted, altered, substituted for, and/or incorporated together without departing from the spirit of the preferred embodiments. For example, a distinct cell impermeable domain may not exist. In such embodiments, other domains accomplish the function of the cell impermeable domain. As another example, the interference domain can be eliminated in certain embodiments wherein two-electrode differential measurements are employed to eliminate interference, for example, one electrode being sensitive to glucose and electrooxidizable interferants and the other only to interferants, such as is described in U.S. Pat. No. 6,514,718. In such embodiments, the interference domain can be omitted.

A variety of configurations are contemplated with the membrane systems of the preferred embodiments, however the exemplary configurations are not meant to be limiting and may be modified within the scope of the preferred embodiments. In one embodiment, the enzyme domain is formed from a material with a high oxygen solubility, which is believed to optimize oxygen availability to the enzyme immobilized therein. In another embodiment, all domains between the fluid supply (for example, interstitial fluid) and the enzyme (up to and including the enzyme domain) are formed from a material with a high oxygen solubility, which is believed to dynamically retain a substantially continuous path of high oxygen availability to the enzyme and/or electroactive surfaces during local ischemic periods. In yet another embodiment, all domains of a membrane system are formed from high oxygen soluble materials; in this way, the membrane system transports and/or maintains high oxygen availability substantially continuously across the membrane system, from the interstitial fluid to the implantable device surface, providing increased oxygen availability to the implantable device, for example electroactive surfaces thereon or transplanted cells located therein. While not wishing to be bound by theory, it is believed that maintaining high oxygen availability at the interface of the implantable device improves device performance even during transient ischemia and other low oxygen situations.

Reference is now made to FIGS. 5A and 5B, which are schematic diagrams of oxygen concentration profiles through a prior art membrane (FIG. 5A) and a membrane system of the preferred embodiments (FIG. 5B). FIG. 5A illustrates a fluid source 52, such as interstitial fluid within the subcutaneous space, which provides fluid to a membrane system 54a. The membrane system 54a is a conventional membrane, for example, formed from a polyurethane-based or other non-high oxygen soluble material. An oxygen-utilizing source 56, such as the immobilized enzyme within the enzyme domain 46 or electroactive surfaces 16 described herein, utilizes oxygen from the fluid as a catalyst or in an electrochemical reaction. In some alternative embodiments, the oxygen-utilizing source 56 comprises cells within a cell transplantation device, which utilize oxygen in the fluid for cellular processes.

The upper dashed lines represent oxygen concentration in the fluid source ($C_f$) and oxygen concentration in the membrane system ($C_m$) at equilibrium (namely, without oxygen utilization) under normal conditions. However, when the membrane system 54a interfaces with an oxygen-utilizing source 56, oxygen concentration within the membrane system will be utilized. Accordingly, line 58a represents oxygen concentration under normal conditions decreasing at steady state as it passes through the membrane system 54a to the oxygen-utilizing source 56. While not wishing to be bound by theory, the oxygen concentration at the interface between the membrane system 54a and the oxygen-utilizing source 56 provides sufficient oxygen under normal conditions for oxygen-utilizing sources in vivo, such as enzymatic reactions, cellular processes, and electroactive surfaces.

Unfortunately, "normal conditions" do not always occur in vivo, for example during transient ischemic periods, such as described in more detail above with reference to FIG. 3. During "ischemic conditions," oxygen concentration is decreased below normal to a concentration as low as zero. Accordingly, line 60a represents oxygen concentration during an ischemic period, wherein the oxygen concentration of the fluid source ($C_f$) is approximately half of its normal concentration. A linear relationship exists between the fluid source oxygen concentration ($C_f$) and the membrane system oxygen concentration ($C_m$) (see Hitchman, M. L. Measurement of Dissolved Oxygen. In *Chemical Analysis*; Elving, P., Winefordner, J., Eds.; John Wiley & Sons: New York, 1978; Vol. 49, pp. 63-70). Accordingly, line 62a represents the oxygen concentration within the membrane system during the ischemic period, which is approximately half of its normal concentration. Unfortunately, the resulting oxygen concentration at the interface of the membrane 54a and oxygen-utilizing source 56 is approximately zero. While not wishing to bound by any particular theory, it is believed that the oxygen concentration at the interface between the conventional membrane system 54a and the oxygen-utilizing source 56 does not provide sufficient oxygen for oxygen-utilizing sources in vivo, such as enzymatic reactions, cellular processes, and electroactive surfaces, during some ischemic conditions.

Referring to FIG. 5B, a fluid source 52, such as interstitial fluid within the subcutaneous space, provides fluid to a membrane system 54b. The membrane system 54b is a membrane system of the preferred embodiments, such as an enzyme domain 46 or an entire membrane system formed from a high oxygen soluble material such as described herein, through which the fluid passes. An oxygen-utilizing source 56, such as the immobilized enzyme described herein, utilizes oxygen from the fluid as a catalyst. In some alternative embodiments, the oxygen-utilizing source 56 comprises cells within a cell transplantation device, which utilize oxygen in the fluid for cellular processes. In some alternative embodiments, the oxygen-utilizing source 56 comprises an electroactive surface that utilizes oxygen in an electrochemical reaction.

The upper dashed lines represent oxygen concentration in the fluid source ($C_f$) and oxygen concentration in the membrane system ($C_m$) at equilibrium (namely, without oxygen utilization) under normal conditions. The membrane system of the preferred embodiments 54b is illustrated with a significantly higher oxygen concentration than the conventional membrane 54a. This higher oxygen concentration at equilibrium is attributed to higher oxygen solubility inherent in the properties of the membrane systems of the preferred embodiments as compared to conventional membrane materials. Line 58b represents oxygen concentration under normal conditions decreasing at steady state as it passes through the membrane system 54b to the oxygen-utilizing source 56. While not wishing to be bound by theory, the oxygen concentration at the interface between the membrane system 54b and the oxygen-utilizing source 56 is believe to provide sufficient oxygen under normal conditions for oxygen-utilizing sources in vivo, such as enzymatic reactions, cellular processes, and electroactive surfaces.

Such as described above, "normal conditions" do not always occur in vivo, for example during transient ischemic periods, wherein oxygen concentration is decreased below normal to a concentration as low as zero. Accordingly, line 60b represents oxygen concentration during ischemic conditions, wherein the oxygen concentration of the fluid source ($C_f$) is approximately half of its normal concentration. Because of the linear relationship between the fluid source oxygen concentration ($C_f$) and the membrane system oxygen concentration ($C_m$), the membrane system oxygen concentration, which is represented by a line 62b, is approximately half of its normal concentration. In contrast to the conventional membrane 62a illustrated in FIG. 5A, however, the high oxygen solubility of the membrane system of the preferred embodiments dynamically retains a higher oxygen availability within the membrane 54b, which can be utilized during ischemic periods to compensate for oxygen deficiency, illustrated by sufficient oxygen concentration 62b provided at the interface of the membrane 54b and oxygen-utilizing source 56. Therefore, the high oxygen solubility of the membrane systems of the preferred embodiments enables device function even during transient ischemic periods.

Methods and devices that are suitable for use in conjunction with aspects of the preferred embodiments are disclosed in co-pending U.S. patent application Ser. No. 10/842,716, filed May 10, 2004 and entitled, "MEMBRANE SYSTEMS INCORPORATING BIOACTIVE AGENTS"; co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/685,636 filed Oct. 28, 2003 and entitled, "SILICONE COMPOSITION FOR MEMBRANE SYSTEM"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. Pat. No. 6,702,857 entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE"; U.S. Appl. No. 60/489,615 filed Jul. 23, 2003 and entitled "ROLLED ELECTRODE ARRAY AND ITS METHOD FOR MANUFACTURE"; U.S. Appl. No. 60/490,010 filed Jul. 25, 2003 and entitled "INCREASING BIAS FOR OXYGEN PRODUCTION IN AN ELECTRODE ASSEMBLY"; U.S. Appl. No. 60/490,208 filed Jul. 25, 2003 and entitled "ELECTRODE ASSEMBLY WITH INCREASED OXYGEN GENERATION"; U.S. Appl. No. 60/490,007 filed Jul. 25, 2003 and entitled "OXYGEN-GENERATING ELECTRODE FOR USE IN ELECTROCHEMICAL SENSORS"; U.S. application Ser. No. 10/896,637 filed on Jul. 21, 2004 and entitled "ROLLED ELECTRODE ARRAY AND ITS METHOD FOR MANUFACTURE"; U.S. application Ser. No. 10/896,772 filed on Jul. 21, 2004 and entitled "INCREASING BIAS FOR OXYGEN PRODUCTION IN AN ELECTRODE ASSEMBLY"; U.S. application Ser. No. 10/897,377 filed on Jul. 21, 2004 and entitled "ELECTRODE ASSEMBLY WITH INCREASED OXYGEN GENERATION"; U.S. application Ser. No. 10/897,312 filed on Jul. 21, 2004 and entitled "ELECTRODE SYSTEMS FOR ELECTROCHEMICAL SENSORS". The foregoing patent applications and patents are incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. An electrochemical sensor for determining a presence or a concentration of an analyte comprising glucose in a fluid, the sensor comprising:
   a membrane system comprising an enzyme domain comprising an enzyme that reacts with the analyte in the fluid as it passes through the enzyme domain; and
   a working electrode comprising a conductive material, wherein the working electrode is configured to measure a product of a reaction of the enzyme with the analyte, wherein the membrane system comprises a resistance domain configured to restrict a flow of the glucose therethrough, wherein the resistance domain comprises:
a silicone with a non-silicone containing hydrophile covalently incorporated or grafted therein,
a polyurethane, or
a copolymer thereof, wherein the polyurethane comprises a polyurethane urea/polyurethane-block-polyethylene glycol blend.

2. The electrochemical sensor of claim 1, wherein the enzyme domain comprises a polymer material with a high oxygen solubility.

3. The electrochemical sensor of claim 2, wherein the polymer material is selected from the group consisting of silicone, fluorocarbon, and perfluorocarbon.

4. The electrochemical sensor of claim 3, wherein the silicone comprises a hydrophile covalently incorporated or grafted therein, the hydrophile comprising a polyethylene glycol, a propylene glycol, a pyrrolidone, an ester, an amide, a carbonate, a polypropylene glycol, or a copolymer thereof.

5. The electrochemical sensor of claim 1, wherein the resistance domain is located more distal to the working electrode than the enzyme domain.

6. The electrochemical sensor of claim 5, wherein the resistance domain further comprises a polymer material selected from the group consisting of fluorocarbon and perfluorocarbon.

7. The electrochemical sensor of claim 1, further comprising a cell impermeable domain that is substantially impermeable to cells, wherein the cell impermeable domain is located more distal to the working electrode than the enzyme domain, and wherein the cell impermeable domain comprises a polymer material with a high oxygen solubility.

8. The electrochemical sensor of claim 7, wherein the cell impermeable domain comprises a material selected from the group consisting of silicone, fluorocarbon, and perfluorocarbon.

9. The electrochemical sensor of claim 8, wherein the silicone comprises a hydrophile covalently incorporated or grafted therein, the hydrophile comprising a polyethylene glycol, a propylene glycol, a pyrrolidone, an ester, an amide, a carbonate, a polypropylene glycol, or a copolymer thereof.

10. The electrochemical sensor of claim 1, further comprising a cell disruptive domain that comprises a substantially porous structure, wherein the cell disruptive domain is located more distal to the working electrode than the enzyme domain, and wherein the cell disruptive domain comprises a polymer material with high oxygen solubility.

11. The electrochemical sensor of claim 10, wherein the cell disruptive domain comprises a polymer material selected from the group consisting of silicone, fluorocarbon, and perfluorocarbon.

12. The electrochemical sensor of claim 1, further comprising an interference domain configured to limit or block interfering species, wherein the interference domain is located more proximal to the working electrode than the enzyme domain, and wherein the interference domain comprises a polymer material with a high oxygen solubility.

13. The electrochemical sensor of claim 12, wherein the interference domain comprises a polymer material selected from the group consisting of silicone, fluorocarbon, and perfluorocarbon.

14. The electrochemical sensor of claim 1, further comprising an electrolyte domain configured to provide hydrophilicity at the working electrode, wherein the electrolyte domain is located more proximal to the working electrode than the enzyme domain, and wherein the electrolyte domain comprises a polymer material with a high oxygen solubility.

15. The electrochemical sensor of claim 14, wherein the electrolyte domain comprises a polymer material selected from the group consisting of silicone, fluorocarbon, and perfluorocarbon.

16. The electrochemical sensor of claim 1, wherein the hydrophile comprises a polyethylene glycol, a propylene glycol, a pyrrolidone, an ester, an amide, a carbonate, a polypropylene glycol, or a copolymer thereof.

17. An electrochemical sensor for determining a presence or a concentration of an analyte comprising glucose in a fluid, the sensor comprising:
a membrane system comprising an enzyme domain comprising an enzyme that reacts with the analyte in the fluid as it passes through the enzyme domain; and
a working electrode comprising a conductive material, wherein the working electrode is configured to measure a product of a reaction of the enzyme with the analyte, wherein the membrane system comprises a resistance domain configured to restrict a flow of the glucose therethrough, wherein the resistance domain comprises:
a silicone with a non-silicone containing hydrophile covalently incorporated or grafted therein,
a polyurethane, or
a copolymer thereof, wherein a thickness of the resistance domain is in a range of from about 15 microns to about 100 microns.

18. The electrochemical sensor of claim 17, wherein the enzyme domain comprises a polymer material with a high oxygen solubility.

19. The electrochemical sensor of claim 18, wherein the polymer material is selected from the group consisting of silicone, fluorocarbon, and perfluorocarbon.

20. The electrochemical sensor of claim 19, wherein the silicone comprises a hydrophile covalently incorporated or grafted therein, the hydrophile comprising a polyethylene glycol, a propylene glycol, a pyrrolidone, an ester, an amide, a carbonate, a polypropylene glycol, or a copolymer thereof.

21. The electrochemical sensor of claim 17, wherein the resistance domain is located more distal to the working electrode than the enzyme domain.

22. The electrochemical sensor of claim 21, wherein the resistance domain further comprises a polymer material selected from the group consisting of fluorocarbon and perfluorocarbon.

23. The electrochemical sensor of claim 17, further comprising a cell impermeable domain that is substantially impermeable to cells, wherein the cell impermeable domain is located more distal to the working electrode than the enzyme domain, and wherein the cell impermeable domain comprises a polymer material with a high oxygen solubility.

24. The electrochemical sensor of claim 23, wherein the cell impermeable domain comprises a material selected from the group consisting of silicone, fluorocarbon, and perfluorocarbon.

25. The electrochemical sensor of claim 24, wherein the silicone comprises a hydrophile covalently incorporated or grafted therein, the hydrophile comprising a polyethylene glycol, a propylene glycol, a pyrrolidone, an ester, an amide, a carbonate, a polypropylene glycol, or a copolymer thereof.

26. The electrochemical sensor of claim 17, further comprising a cell disruptive domain that comprises a substantially porous structure, wherein the cell disruptive domain is located more distal to the working electrode than the enzyme domain, and wherein the cell disruptive domain comprises a polymer material with high oxygen solubility.

27. The electrochemical sensor of claim 26, wherein the cell disruptive domain comprises a polymer material selected from the group consisting of silicone, fluorocarbon, and perfluorocarbon.

28. The electrochemical sensor of claim 17, further comprising an interference domain configured to limit or block interfering species, wherein the interference domain is located more proximal to the working electrode than the enzyme domain, and wherein the interference domain comprises a polymer material with a high oxygen solubility.

29. The electrochemical sensor of claim 28, wherein the interference domain comprises a polymer material selected from the group consisting of silicone, fluorocarbon, and perfluorocarbon.

30. The electrochemical sensor of claim 17, further comprising an electrolyte domain configured to provide hydrophilicity at the working electrode, wherein the electrolyte domain is located more proximal to the working electrode than the enzyme domain, and wherein the electrolyte domain comprises a polymer material with a high oxygen solubility.

31. The electrochemical sensor of claim 30, wherein the electrolyte domain comprises a polymer material selected from the group consisting of silicone, fluorocarbon, and perfluorocarbon.

32. The electrochemical sensor of claim 17, wherein the hydrophile comprises a polyethylene glycol, a propylene glycol, a pyrrolidone, an ester, an amide, a carbonate, a polypropylene glycol, or a copolymer thereof.

33. An electrochemical sensor for determining a presence or a concentration of an analyte comprising glucose in a fluid, the sensor comprising:
 a membrane system comprising an enzyme domain comprising an enzyme that reacts with the analyte in the fluid as it passes through the enzyme domain; and
 a working electrode comprising a conductive material, wherein the working electrode is configured to measure a product of a reaction of the enzyme with the analyte,
 wherein the membrane system comprises a resistance domain configured to restrict a flow of the glucose therethrough, wherein the resistance domain comprises:
  a silicone with a non-silicone containing hydrophile covalently incorporated or grafted therein,
  a polyurethane, or
  a copolymer thereof, wherein a thickness of the resistance domain is in a range of from about 45 microns to about 60 microns.

34. The electrochemical sensor of claim 33, wherein the enzyme domain comprises a polymer material with a high oxygen solubility.

35. The electrochemical sensor of claim 34, wherein the polymer material is selected from the group consisting of silicone, fluorocarbon, and perfluorocarbon.

36. The electrochemical sensor of claim 33, wherein the resistance domain is located more distal to the working electrode than the enzyme domain.

37. The electrochemical sensor of claim 35, wherein the silicone comprises a hydrophile covalently incorporated or grafted therein, the hydrophile comprising a polyethylene glycol, a propylene glycol, a pyrrolidone, an ester, an amide, a carbonate, a polypropylene glycol, or a copolymer thereof.

38. The electrochemical sensor of claim 36, wherein the resistance domain further comprises a polymer material selected from the group consisting of fluorocarbon and perfluorocarbon.

39. The electrochemical sensor of claim 33, further comprising a cell impermeable domain that is substantially impermeable to cells, wherein the cell impermeable domain is located more distal to the working electrode than the enzyme domain, and wherein the cell impermeable domain comprises a polymer material with a high oxygen solubility.

40. The electrochemical sensor of claim 39, wherein the cell impermeable domain comprises a material selected from the group consisting of silicone, fluorocarbon, and perfluorocarbon.

41. The electrochemical sensor of claim 40, wherein the silicone comprises a hydrophile covalently incorporated or grafted therein, the hydrophile comprising a polyethylene glycol, a propylene glycol, a pyrrolidone, an ester, an amide, a carbonate, a polypropylene glycol, or a copolymer thereof.

42. The electrochemical sensor of claim 33, further comprising a cell disruptive domain that comprises a substantially porous structure, wherein the cell disruptive domain is located more distal to the working electrode than the enzyme domain, and wherein the cell disruptive domain comprises a polymer material with high oxygen solubility.

43. The electrochemical sensor of claim 42, wherein the cell disruptive domain comprises a polymer material selected from the group consisting of silicone, fluorocarbon, and perfluorocarbon.

44. The electrochemical sensor of claim 33, further comprising an interference domain configured to limit or block interfering species, wherein the interference domain is located more proximal to the working electrode than the enzyme domain, and wherein the interference domain comprises a polymer material with a high oxygen solubility.

45. The electrochemical sensor of claim 44, wherein the interference domain comprises a polymer material selected from the group consisting of silicone, fluorocarbon, and perfluorocarbon.

46. The electrochemical sensor of claim 33, further comprising an electrolyte domain configured to provide hydrophilicity at the working electrode, wherein the electrolyte domain is located more proximal to the working electrode than the enzyme domain, and wherein the electrolyte domain comprises a polymer material with a high oxygen solubility.

47. The electrochemical sensor of claim 46, wherein the electrolyte domain comprises a polymer material selected from the group consisting of silicone, fluorocarbon, and perfluorocarbon.

48. The electrochemical sensor of claim 33, wherein the hydrophile comprises a polyethylene glycol, a propylene glycol, a pyrrolidone, an ester, an amide, a carbonate, a polypropylene glycol, or a copolymer thereof.

49. An electrochemical sensor for determining a presence or a concentration of an analyte comprising glucose in a fluid, the sensor comprising:
 a membrane system comprising an enzyme domain comprising an enzyme that reacts with the analyte in the fluid as it passes through the enzyme domain; and
 a working electrode comprising a conductive material, wherein the working electrode is configured to measure a product of a reaction of the enzyme with the analyte,
 wherein the membrane system comprises a resistance domain configured to restrict a flow of the glucose therethrough, wherein the resistance domain comprises:

a silicone with a non-silicone containing hydrophile covalently incorporated or grafted therein,
a polyurethane, or
a copolymer thereof, having an oxygen permeability in a range of from about 1 Barrers to about 1000 Barrers.

50. The electrochemical sensor of claim 49, wherein the enzyme domain comprises a polymer material with a high oxygen solubility.

51. The electrochemical sensor of claim 50, wherein the polymer material is selected from the group consisting of silicone, fluorocarbon, and perfluorocarbon.

52. The electrochemical sensor of claim 51, wherein the silicone comprises a hydrophile covalently incorporated or grafted therein, the hydrophile comprising a polyethylene glycol, a propylene glycol, a pyrrolidone, an ester, an amide, a carbonate, a polypropylene glycol, or a copolymer thereof.

53. The electrochemical sensor of claim 49, wherein the resistance domain is located more distal to the working electrode than the enzyme domain.

54. The electrochemical sensor of claim 53, wherein the resistance domain further comprises a polymer material selected from the group consisting of fluorocarbon and perfluorocarbon.

55. The electrochemical sensor of claim 49, further comprising a cell impermeable domain that is substantially impermeable to cells, wherein the cell impermeable domain is located more distal to the working electrode than the enzyme domain, and wherein the cell impermeable domain comprises a polymer material with a high oxygen solubility.

56. The electrochemical sensor of claim 55, wherein the cell impermeable domain comprises a material selected from the group consisting of silicone, fluorocarbon, and perfluorocarbon.

57. The electrochemical sensor of claim 56, wherein the silicone comprises a hydrophile covalently incorporated or grafted therein, the hydrophile comprising a polyethylene glycol, a propylene glycol, a pyrrolidone, an ester, an amide, a carbonate, a polypropylene glycol, or a copolymer thereof.

58. The electrochemical sensor of claim 49, further comprising a cell disruptive domain that comprises a substantially porous structure, wherein the cell disruptive domain is located more distal to the working electrode than the enzyme domain, and wherein the cell disruptive domain comprises a polymer material with high oxygen solubility.

59. The electrochemical sensor of claim 58, wherein the cell disruptive domain comprises a polymer material selected from the group consisting of silicone, fluorocarbon, and perfluorocarbon.

60. The electrochemical sensor of claim 49, further comprising an interference domain configured to limit or block interfering species, wherein the interference domain is located more proximal to the working electrode than the enzyme domain, and wherein the interference domain comprises a polymer material with a high oxygen solubility.

61. The electrochemical sensor of claim 60, wherein the interference domain comprises a polymer material selected from the group consisting of silicone, fluorocarbon, and perfluorocarbon.

62. The electrochemical sensor of claim 49, further comprising an electrolyte domain configured to provide hydrophilicity at the working electrode, wherein the electrolyte domain is located more proximal to the working electrode than the enzyme domain, and wherein the electrolyte domain comprises a polymer material with a high oxygen solubility.

63. The electrochemical sensor of claim 62, wherein the electrolyte domain comprises a polymer material selected from the group consisting of silicone, fluorocarbon, and perfluorocarbon.

64. The electrochemical sensor of claim 49, wherein the hydrophile comprises a polyethylene glycol, a propylene glycol, a pyrrolidone, an ester, an amide, a carbonate, a polypropylene glycol, or a copolymer thereof.

* * * * *

UNITED STATES PATENT AND TRADEMARK OFFICE
CERTIFICATE OF CORRECTION

PATENT NO. : 10,610,140 B2
APPLICATION NO. : 15/977927
DATED : April 7, 2020
INVENTOR(S) : James R. Petisce et al.

It is certified that error appears in the above-identified patent and that said Letters Patent is hereby corrected as shown below:

On the Title Page

On Page 3, Column 1, Item (56), Line 58, under U.S. Patent Documents, delete "Schaffer" and insert --Schaffar--.

On Page 3, Column 1, Item (56), Line 68, under U.S. Patent Documents, delete "Priedel" and insert --Preidel--.

On Page 3, Column 2, Item (56), Line 15, under U.S. Patent Documents, delete "Shen" and insert --Sheu--.

On Page 6, Column 1, Item (56), Line 29, under Foreign Patent Documents, delete "91238319" and insert --61238319--.

On Page 6, Column 2, Item (56), Line 30, under Other Publications, delete "subcutanecus" and insert --subcutaneous--.

On Page 7, Column 1, Item (56), Line 33, under Other Publications, delete "Surfacts" and insert --Surfaces--.

On Page 7, Column 2, Item (56), Line 19, under Other Publications, delete "far" and insert --for--.

On Page 7, Column 2, Item (56), Line 22, under Other Publications, delete "Corresion" and insert --Corrosion--.

On Page 7, Column 2, Item (56), Line 39, under Other Publications, delete "(3" and insert --3--.

On Page 7, Column 2, Item (56), Line 71, under Other Publications, delete "technology." and insert --technology--.

Signed and Sealed this
Twenty-first Day of July, 2020

Andrei Iancu
*Director of the United States Patent and Trademark Office*

CERTIFICATE OF CORRECTION (continued)
U.S. Pat. No. 10,610,140 B2

On Page 8, Column 2, Item (56), Line 45, under Other Publications, delete "diabetes." and insert --diabetes--.

On Page 8, Column 2, Item (56), Line 62, under Other Publications, delete "Eleotrochemical" and insert --Electrochemical--.

On Page 8, Column 2, Item (56), Line 66, under Other Publications, delete "Eleotrode." and insert --Electrode.--.

On Page 9, Column 1, Item (56), Line 31, under Other Publications, delete "Coimmoblized" and insert --Coimmobilized--.

On Page 9, Column 1, Item (56), Line 53, under Other Publications, delete "potentiaiiy" and insert --Potentially--.

On Page 9, Column 2, Item (56), Line 15, under Other Publications, delete "B iosensors" and insert --Biosensors--.

On Page 9, Column 2, Item (56), Line 41, under Other Publications, delete "1996." and insert --1996,--.

On Page 9, Column 2, Item (56), Line 63, under Other Publications, delete "Electronanalysis" and insert --Electroanalysis--.

On Page 10, Column 1, Item (56), Line 16, under Other Publications, delete "research." and insert --research--.

On Page 10, Column 1, Item (56), Line 50, under Other Publications, delete "glucoseoxidase" and insert --glucose oxidase--.

On Page 10, Column 2, Item (56), Line 43, under Other Publications, delete "Solution" and insert --117 Solution--.

On Page 10, Column 2, Item (56), Line 57, under Other Publications, delete "(I-" and insert --(L- --.

On Page 10, Column 2, Item (56), Line 60, under Other Publications, delete "(3" and insert --3--.

On Page 11, Column 1, Item (56), Line 16, under Other Publications, delete "Bromedical" and insert --Biomedical--.

On Page 11, Column 1, Item (56), Line 68, under Other Publications, delete "216." and insert --218.--.

On Page 11, Column 2, Item (56), Line 17, under Other Publications, delete "cem" and insert --chem--.

CERTIFICATE OF CORRECTION (continued)
U.S. Pat. No. 10,610,140 B2

On Page 11, Column 2, Item (56), Line 48, under Other Publications, delete "Matl" and insert --Mater--.

On Page 12, Column 1, Item (56), Line 15, under Other Publications, delete "earable" and insert --Wearable--.

On Page 12, Column 1, Item (56), Line 18, under Other Publications, delete "Future" and insert --Futura--.

On Page 12, Column 1, Item (56), Line 22, under Other Publications, delete "D iabetologia" and insert --Diabetologia--.

On Page 12, Column 1, Item (56), Line 59, under Other Publications, delete "Continous" and insert --Continuous--.

On Page 12, Column 2, Item (56), Line 46, under Other Publications, delete "D iabetes" and insert --Diabetes--.

On Page 12, Column 2, Item (56), Line 69, under Other Publications, delete "Biochim." and insert --Biochem.--.

In the Specification

In Column 4, Line 23, delete "andrenostenedione;" and insert --androstenedione;--.

In Column 4, Line 39, delete "diptheria" and insert --diphtheria--.

In Column 4, Line 46, delete "perioxidase" and insert --peroxidase--.

In Column 4, Line 55, delete "sissomicin;" and insert --sisomicin;--.

In Column 4, Line 59, delete "duodenalisa," and insert --duodenalis,--.

In Column 4, Line 67, delete "Trepenoma pallidium," and insert --Treponema pallidum,--.

In Column 5, Line 1, delete "stomatis" and insert --stomatitis--.

In Column 5, Line 22, delete "(barbituates," and insert --(barbiturates,--.

In Column 5, Line 38, delete "(FHIAA)." and insert --(5-HIAA).--.

In Column 5, Line 60, delete "by product" and insert --byproduct--.

In Column 5, Line 65, delete "02" and insert --$O_2$--.

CERTIFICATE OF CORRECTION (continued)
U.S. Pat. No. 10,610,140 B2

In Column 8, Line 19, delete "Caduff;" and insert --Cardiff;--.

In Column 12, Line 46, delete "cm/cm$^2$ s" and insert --cm/cm$^2$s--.